US008642515B2

(12) United States Patent  (10) Patent No.: US 8,642,515 B2
Kidd  (45) Date of Patent: Feb. 4, 2014

(54) GENETIC DETERMINANTS OF PROSTATE CANCER RISK

(75) Inventor: La Creis Renee Kidd, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/393,402

(22) PCT Filed: Aug. 27, 2010

(86) PCT No.: PCT/US2010/046988
§ 371 (c)(1),
(2), (4) Date: Apr. 30, 2012

(87) PCT Pub. No.: WO2011/028642
PCT Pub. Date: Mar. 10, 2011

(65) Prior Publication Data
US 2012/0220467 A1  Aug. 30, 2012

Related U.S. Application Data

(60) Provisional application No. 61/240,089, filed on Sep. 4, 2009.

(51) Int. Cl.
*C40B 20/00* (2006.01)
*C40B 40/06* (2006.01)

(52) U.S. Cl.
USPC .......................................... 506/16; 435/6.11

(58) Field of Classification Search
USPC ............................................................ 506/4
See application file for complete search history.

(56) References Cited

U.S. PATENT DOCUMENTS

| | | | |
|---|---|---|---|
| 6,194,454 B1 * | 2/2001 | Dow | 514/522 |
| 6,811,779 B2 | 11/2004 | Rockwell et al. | |
| 7,056,509 B2 | 6/2006 | Thorpe et al. | |
| 7,169,901 B2 | 1/2007 | Baca et al. | |
| 7,297,334 B2 | 11/2007 | Baca et al. | |
| 2002/0032315 A1 | 3/2002 | Baca et al. | |
| 2007/0207486 A1 | 9/2007 | Lenz | |
| 2008/0009419 A1 | 1/2008 | Ralph et al. | |
| 2008/0187966 A1 | 8/2008 | Simmons | |
| 2009/0010883 A1 | 1/2009 | Fyfe et al. | |
| 2010/0184773 A1 | 7/2010 | Lenz | |

FOREIGN PATENT DOCUMENTS

| | | |
|---|---|---|
| WO | WO9410202 A1 | 5/1994 |
| WO | WO9421679 A1 | 9/1994 |
| WO | WO2006135117 A1 | 12/2006 |

OTHER PUBLICATIONS

Stadler et al., "A Randomized Phase II Trial of the Antiangiogenic Agent SU5416 in Hormone-Refractory Prostate Cancer", Clinical Cancer Research, vol. 10, p. 3365-3370 (2004).*
The ATBC Cancer Prevention Study Group, "The Alpha-Tocopherol, Beta-Carotene Lung Cancer Prevention Study: Design, Methods, Participant Characteristics, and Compliance", Annals of Epidemiology, vol. 4, No. 1, p. 1-10 (1994).*
Kidd et al., "Sequence Variation Within the 5' Regulatory Regions of the Vitamin D Binding Protein and Receptor Genes and Prostate Cancer Risk", The Prostate, vol. 64, p. 272-282, (2005).*
Page et al., "Heredity and Prostate Cancer: A Study of World War II Veteran Twins", The Prostate, vol. 33, p. 240-245 (1997).*
Michaelson et al., "Phase II study of sunitinib in men with advanced prostate cancer", Annals of Oncology, vol. 20, p. 913-920 (May 2009).*
Sfar et al., "Association of VEGF genetic polymorphisms with prostate carcinoma risk and clinical outcome", Cytokine, vol. 35, p. 21-28 (2006).*
Yamamori et al., "Association of VEGF genotype with mRNA level in colorectal adenocarcinomas", Biochemical and Biophysical Research Communications, vol. 325, p. 144-150 (2004).*
http://www.ncbi.nlm.nih.gov/projects/SNP/snp_ref. cgi?rs=3025040; 2001.
http://www.ncbi.nlm.nih.gov/projects/SNP/snp_ref. cgi?rs=7692791; 2003.
Balkwill et al; Inflammation and cancer: back to Virchow?; Lancet; 2001; pp. 357:539-545.
Beebe et al; Pharmacological Characterization of CP-547,632, a Novel Vascular Endothelial Growth Factor Receptor-2 Tyrosine Kinase Inhibitor for Cancer Therapy; Cancer Research; 2003; pp. 63:7301-7309.
Berthon et al; Predisposing gene for early-onset prostate cancer, localized on chromosome 1q42.2-43; Am. J. Hum. Genet.; 1998; pp. 62:1416-1424.
Brekken et al; Vascular Endothelial Growth Factor as a Marker of Tumor Endothelium; Cancer Research; 1998; pp. 58:1952-1959.
Carmeliet et al; Angiogenesis in cancer and other diseases; Nature; 2000; pp. 407:249-257.
Carmeliet et al; Angiogenesis in life, disease and medicine; Nature; 2005; pp. 438:932-936.
Chen et al; A systematic analysis of disease-associated variants in the 3' regulatory regions of human protein-coding genes II: the importance of mRNA secondary structure in assessing the functionality of 3'UTR variants; Hum. Genet.; 2006; pp. 120:301-333.
Claffey et al; Regulation of VEGF/VPF expression in tumor cells: consequences for tumor growth and metastasis; Cancer Metastasis Rev.; 1996; pp. 15:165-176.
Derynck et al; TGF-beta signaling in tumor suppression and cancer progression; Nat. Genet.; 2001; pp. 29:117-129.
Doi et al; Functional Polymorphisms in the Vascular Endothelial Growth Factor Gene are associated with Development of End-Stage Renal Disease in Males; J. Am. Soc. Nephrol.; 2006; pp. 17:823-830.
Dunning et al; A transforming growth factor beta 1 signal peptide variant increases secretion in vitro and is associated with increased incidence of invasive breast cancer; Cancer Res.; 2003; pp. 63:2610-2615.
Ewart-Toland et al; A gain of function TGFB1 polymorphism may be associated with late stage prostate cancer; Cancer Epidemiol. Biomarkers; 2004; pp. 13:759-764.

(Continued)

*Primary Examiner* — Stephanie K Mummert
*Assistant Examiner* — Jonah Smith
(74) *Attorney, Agent, or Firm* — Fish & Richardson P.C.

(57) ABSTRACT

Described are methods of determining if a subject has a genetic predisposition to developing prostate cancer (PCa).

13 Claims, 3 Drawing Sheets

(56) References Cited

OTHER PUBLICATIONS

Faupel-Badger et al; Association of IL-10 polymorphisms with prostate cancer risk and grade of disease; Cancer Causes Control; 2008; pp. 19:119-124.
Ferrara et al; The biology of VEGF and its receptors; Nat. Med.; 2003; pp. 9:669-676.
Ferrara; VEGF and the quest for tumour angiogenesis factors; Nat. Rev. Cancer; 2002; pp. 2:795-803.
Ford et al; Risks of cancer in BRCA1-mutation carriers. Breast Cancer Linkage Consortium; Lancet; 1994; pp. 343:692-695.
Gibbs et al; Evidence for a rare prostate cancer-susceptibility locus at chromosome 1p36; Am. J. Hum. Genet.; 1999; pp. 64:776-787.
Goodman et al; Approval Summary: Sunitinib for the Treatment of Imatinib Refractory or Intolerant Gastrointestinal Stromal Tumors and Advanced Renal Cell Carcinoma; Clin. Cancer Res.; 2007; pp. 13:1367-1373.
Grainger et al; Genetic control of the circulating concentration of transforming growth factor type beta 1; Hum. Mol. Genet.; 1999; pp. 8:93-97.
Green et al; Expression of vascular endothelial growth factor (VEGF) in locally invasive prostate cancer is prognostic for radiotherapy outcome; Int. J. Radiat. Oncol. Biol. Phys.; 2007; pp. 67:84-90.
Holash et al; VEGF-Trap: A VEGF blocker with potent antitumor effects; PNAS; 2002; pp. 99(17):11393-11398.
Houck et al; The vascular endothelial growth factor family: identification of a fourth molecular species and characterization of alternative splicing of RNA; Mol. Endocrinol.; 1991; pp. 5:1806-1814.
Howell et al; IL-10 promoter polymorphisms influence tumour development in cutaneous malignant melanoma; Genes Immun.; 2001; pp. 2:25-31.
Huang et al; Interleukin 10 suppresses tumor growth and metastasis of human melanoma cells: potential inhibition of angiogenesis; Clin. Cancer Res.; 1996; pp. 2:1969-1979.
Hurwitz et al; Bevacizumab plus Irinotecan, Fluorouracil, and Leucovorin for Metastatic Colorectal Cancer; The New England Journal of Medicine; 2004; pp. 350(23):2335-2342.
Jacobs et al; Polymorphisms in Angiogenesis-Related Genes and Prostate Cancer; Cancer Epidemiol. Biomarkers Prev.; 2008; pp. 17:972-977.
Kane et al; Sorafenib for the Treatment of Advanced Renal Cell Carcinoma; Clin. Cancer Res.; 2006; pp. 12:7271-7278.
Kaya et al; The prognostic significance of vascular endothelial growth factor levels in sera of non-small cell lung cancer patients; Respir. Med.; 2004; pp. 98:632-636.
Kim et al; Evidence of the neuron-restrictive silencer factor (NRSF) interaction with Sp3 and its synergic repression to the mu opioid receptor (MOR) gene; Nucleic Acids Res.; 2006; pp. 34:6392-6403.
Kollermann et al; Expression of vascular endothelial growth factor (VEGF) and VEGF receptor Flk-1 in benign, premalignant, and malignant prostate tissue; Am. J. Clin. Pathol.; 2001; pp. 116:115-121.
Krippl et al; A common 936 C/T gene polymorphism of vascular endothelial growth factor is associated with decreased breast cancer risk; Int. J. Cancer; 2003; pp. 106:468-471.
Krippl et al; The L10P polymorphism of the transforming growth factor-beta 1 gene is not associated with breast cancer risk; Cancer Lett.; 2003; pp. 201:181-184.
Lei et al; Identification and characterization of a new splicing variant of vascular endothelial growth factor: VEGF183; Biochim Biophys Acta; 1998; pp. 1443:400-406.
Leung et al; Vascular endothelial growth factor is a secreted angiogenic mitogen; Science; 1989; pp. 246:1306-1309.
Lichtenstein et al; Environmental and heritable factors in the causation of cancer—analyses of cohorts of twins from Sweden, Denmark, and Finland; N. Engl. J. Med.; 2000; pp. 343:78-85.
Lu et al; Association of genetic polymorphisms in the VEGF gene with breast cancer survival; Cancer Res.; 2005; pp. 65:5015-5019.
Michaud et al; Genetic polymorphisms of interleukin-1B (IL-1B), IL-6, IL-8, and IL-10 and risk of prostate cancer; Cancer Res.; 2006; pp. 66:4525-4530.

Nabioullin et al; Interleukin-10 is a potent inhibitor of tumor cytotoxicity by human monocytes and alveolar macrophages; J. Leukoc. Biol.; 1994; pp. 55:437-442.
Odedina et al; Prostate cancer disparities in Black men of African descent: a comparative literature review of prostate cancer burden among Black men in the United States, Caribbean, United Kingdom, and West Africa; Infect. Agents Can.; 2009; pp. 4(Suppl 1):S2(pp. 1-8).
Park et al; Association between genetic variations of vascular endothelial growth factor receptor 2 and atopy in the Korean population; J. Allergy Clin. Immunol.; 2006; pp. 117:774-779.
Peyromaure et al; The expression of vascular endothelial growth factor is associated with the risk of cancer progression after radical prostatectomy; BJU Int.; 2007; pp. 99:1150-1153.
Plaisance et al; The repressor element silencing transcription factor (REST)-mediated transcriptional repression requires the inhibition of Sp1; J. Biol. Chem.; 2005; pp. 280:401-407.
Poltorak et al; VEGF145, a secreted vascular endothelial growth factor isoform that binds to extracellular matrix; J. Biol. Chem.; 1997; pp. 272:7151-7158.
Presta et al; Humanization of an anti-vascular endothelial growth factor monoclonal antibody for the therapy of solid tumors and other disorders; Cancer Res.; 1997; pp. 57:4593-4599.
Quinn et al; Fetal liver kinase 1 is a receptor for vascular endothelial growth factor and is selectively expressed in vascular endothelium; Proc. Natl. Acad. Sci. USA; 1993; pp. 90:7533-7537.
Renner et al; A common 936 C/T mutation in the gene for vascular endothelial growth factor is associated with vascular endothelial growth factor plasma levels; J. Vasc. Res.; 2000; pp. 37:443-448.
Richter et al; Interleukin 10 transfected into Chinese hamster ovary cells prevents tumor growth and macrophage infiltration; Cancer Res.; 1993; pp. 53:4134-4137.
Robinson et al; The splice variants of vascular endothelial growth factor (VEGF) and their receptors; J. Cell Sci.; 2001; pp. 114:853-865.
Ruggeri et al; CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models; Cancer Research; 2003; 63:5978-5991.
Schlaeppi et al; Targeting Vascular Endothelial Growth Factor (VEGF) for Anti-Tumor Therapy, by Anti-VEGF Neutralizing Monoclonal Antibodies or by VEGF Receptor Tyrosine-Kinase Inhibitors; Cancer and Metastasis Rev.; 1999; 18:473-481.
Sfar et al; Association of VEGF genetic polymorphisms with prostate carcinoma risk and clinical outcome; Cytokine; 2006; 35:21-28.
Shahbazi et al; Vascular endothelial growth factor gene polymorphisms are associated with acute renal allograft rejection; J. Am. Soc. Nephrol.; 2002; 13:260-264.
Smith et al; Major susceptibility locus for prostate cancer on chromosome 1 suggested by a genome-wide search; Science; 1996; 274:1371-1374.
Stearns et al; Antimestatic and antitumor activities of interleukin 10 in transfected human prostate PC-3 ML clones: Orthotopic growth in severe combined immunodeficient mice; Clin. Cancer Res.; 1998; 4:2257-2263.
Tavtigian et al; A candidate prostate cancer susceptibility gene at chromosome 17p.; Nat. Genet. ; 2001; 27:172-180.
Tischer et al; The human gene for vascular endothelial growth factor. Multiple protein forms are encoded through alternative exon splicing; J. Biol. Chem.; 1991; 266:11947-11954.
Ton et al; Phase I Evaluation of CDP791, a PEGylated Di-Fab' Conjugate that Binds Vascular Endothelial Growth Factor Receptor 2; Cancer Res.; 2007; 13:7113-7118.
Turner et al; An investigation of polymorphism in the interleukin-10 gene promoter; Eur. J. Immunogenet.; 1997; 24:1-8.
Vancleave et al; Interaction Among Variant Vascular Endothelial Growth Factor (VEGF) and its Receptor in Relation to Prostate Cancer Risk; The Prostate; 2009; 70:341-352.
Waltenberger et al; Different signal transduction properties of KDR and Flt1, two receptors for vascular endothelial growth factor; J. Biol. Chem.; 1994; 269:26988-26995.
Wood et al; PTK787/ZK 222584, a Novel and Potent Inhibitor of Vascular Endothelial Growth Factor Receptor Tyrosine Kinases,

(56) References Cited

OTHER PUBLICATIONS

Impairs Vascular Endothelial Growth Factor-induced Responses and Tumor Growth after Oral Administration; Cancer Research; 2000; 60:2178-2189.

Xu et al; Evidence for a prostate cancer susceptibility locus on the X chromosome; Nat. Genet.; 1998; 20:175-179.

Yamamori et al; Associate of VEGF genotype with mRNA level in colorectal adenocarcinomas; Biochemical and Biophysical Research Communications; 2004; 325:144-150.

Yokota et al; Association of a T29—>C polymorphism of the transforming growth factor-beta1 gene with genetic susceptibility to myocardial infarction in Japanese; Circulation; 2000; 101:2783-2787.

International Search Report and Written Opinion; Young, Lee W.; Feb. 4, 2011; World Intellectual Property Organization (WIPO) (International Bureau of); PCT/US10/46988.

Zahnow et al; CCAAT/enhancer-binding protein beta: its role in breast cancer and associations with receptor tyrosine kinases; Expert Rev. Mol. Med.; 2009; 11:e12.

Zhang et al; A monoclonal antibody that blocks VEGF binding to VEGFR2 (KDR/Flk-1) inhibits vascular expression of Flk-1 and tumor growth in an orthotopic human breast cancer model; Angiogenesis; 2002; 5:35-44.

* cited by examiner

| Gene | rs Number | Nucleotide Change | Nucleic Acid Sequence | Seq ID No. |
|---|---|---|---|---|
| IL10 -1082 | rs1800896 | G>A | ACAACACTACTAAGGCTTCTTTGGGAA[A/G]GGGGAAGTAGGGATAGGTAAGAGGA | 1 |
| IL10 - 819 | rs1800871 | C>T | GGTGTACCCTTGTACAGGTGATGTAA[C/T]ATCTCGTGTGCCTCAGTTTGCTCACT | 2 |
| IL10 - 592 | rs1800872 | C>A | GGAACACATCCTGTGACCCCGCCTGT[A/C]CTGTAGGAAGCCAGTCTCTGGAAAG | 3 |
| IL-10R-153 | rs2256111 | A>G | CTAGCCAGGCCCAAGATGGCCCCGC[A/G]AATGACACATATGAAAGCATCTTCA | 4 |
| IL-10R Ex7-109 | rs9610 | G>A | AGAATAATGACTGACTTGTCTAATTC[A/G]TAGGGATGTGAGGTTCTGCTGAGGA | 5 |
| IL-10R Ex7 241 | rs2229113 | A>G | CCCAGGCTGACAGAACGCTGGGAAAC[A/G]GGGAGCCCCTGTGCTGGGGACAG | 6 |
| TGFB1-509 | rs1800469 | C>T | GTGTCTGCCTCCTGACCCTTCCATCC[C/T]TCAGGTGTCTCCTGTTGCCCCCTCCTC | 7 |
| TGFB1 896 | rs1982 073 rs1800470 | T>C | GCCGCCCTCCCGGGCTGCGGCTGCTGC[C/T]GCTGCTACCGCTGCGTGGCTA | 8 |
| TGFβR1 Ex9+195 | rs868 | A>G | CTCCTGGGTTTAATTTGGAGGTCA[A/G]TTGTTCTACCTCACTGAGAGGGAAC | 9 |
| VEGF 2482 | rs3025040 | C>T | GACAGATACACAGGTACAGGATGAGGACAC[C/T]CTCTGACCAGGAGTTTGG GGAGCTTCAG | 10 |
| VEGF -2578 | rs699947 | C>A | GCTATGCCAGCTGTAGGCCAGACCCTGGCA[A/C]ATCTGGGTGGATAATCAGACTGACTGGTC | 11 |
| VEGF +889 | rs2305948 | G>A | GTACAATCCTTGGTCACTCCGGGTTA[C/T]ACCATCTATAGTTAAGGTGCTCAAA | 12 |
| VEGFR+1 416 | rs1870377 | T>A | GGGTATGGGTTGTCACTGAGACAGC[A/T]GGCTATAAGAAGAGATAACAGGG | 13 |
| VEGFR IVS25- 92 | rs1531289 | G>A | ATCCTTATTTATTAGCATCTCACC[C/G|C/A/G]GCTCTTTACAAATGTGTACTCATTT | 14 |
| VEGFR IVS6+54 | rs7692791 | A>G | GGCCCCTATCTCTCAAGCAAACTTCA[C/T]TGGGGCTTATTATCTAAGTATTGG | 15 |

FIG. 2

| SNP | | PRIMER‡, 5' → 3' (SEQ ID NO) | PROBE‡‡ 5' → 3' (SEQ ID NO) | |
|---|---|---|---|---|
| IL10 -592 | F | agcagcccctccattttactttc (16) | FAM-ttcctacagGacaggc-MGB (32) | (for -592C, wt) |
| | R | gcctgaaccacatcctgtga (17) | VIC-cttcctacagTacaggc-MGB (33) | (for -592A, var) |
| IL-10R Ex7 -241 | F | agatcccgctgtctgtgctatt (18) | FAM-ctcccCgtttccca-MGB (34) | (for Ex7-241G, wt) |
| | R | gcagactgaaagagccccagtt (19) | VIC-ctcccTgtttcccagc-MGB (35) | (for Ex7-241A, var) |
| TGFβ1 896 | F | ccaggcgtcagcaccagta (20) | FAM-tagcagcagcAgcagcagccg-TAMRA (35) | (for 896T, var) |
| | R | ccaccacaccagccctgtt (21) | VIC-tagcagcagcGgcagcagcc-TAMRA (36) | (for 896C, wt) |
| VEGF -1154 | F | ccgctaccagccgacttta (22) | FAM-cctcagcccCtcca--MGB (37) | (for -1154G, wt) |
| | R | gcgggccaggcttca (23) | VIC-cctcagcccTtcca-MGB (38) | (for -1154A, var) |
| VEGFR2 889 | F | tgctgcacagtgtacaatcc (24) | FAM-ctccggttaTaccat-MGB (39) | (for 889A, var) |
| | R | cagtctgggagtgagatgaagaaa (25) | VIC-cggttaCaccatcta-MGB (40) | (for 889G, wt) |
| VEGFR2 1416 | F | tcataatatgcgctgttatctctttctt (26) | FAM-tagccaAgctgtctca-MGB (41) | (for 1416T, wt) |
| | R | cctccacacttctctccattcttca (27) | VIC-tagccaTgctgtctc-MGB (42) | (for 1416A, var) |
| VEGFR2 IVS6+54 | F | attcaaagccagacctccaaatact (28) | FAM-aagccccaGtgaagt-MGB (43) | (for IVS6+54G, var) |
| | R | gaggccctatctctcaagca (29) | VIC-agccccaAtgaagt-MGB (44) | (for IVS6+54A, wt) |
| VEGFR2 IVS25-92 | F | tggagtatgggactctgtgtcttaca (30) | FAM-cctcgtcGgctct-MGB (45) | (for IVS25-92G, wt) |
| | R | cctctttcttcctgaatgctgaa (31) | VIC-ctcgtcAgctcttta-MGB (46) | (for IVS25-92A, var) |

GENETIC DETERMINANTS OF PROSTATE CANCER RISK

CLAIM OF PRIORITY

This application is a §371 National Stage Application of International Patent Application No. PCT/US2010/046988, filed on Aug. 27, 2010, and claims the benefit of U.S. Provisional Patent Application Ser. No. 61/240,089, filed on Sep. 4, 2009, the entire contents of which are hereby incorporated by reference.

TECHNICAL FIELD

This invention relates to methods for predicting risk of developing prostate cancer using genetic variants in the Vascular Endothelial Growth Factor (VEGF) and VEGF Receptor (VEGFR) genes.

BACKGROUND

The American Cancer Society estimates 186,320 men will be diagnosed with prostate cancer (PCa) and 28,660 will die from the disease in 2008. The risk of developing PCa increases with age, family history, and race/ethnicity. Other risk factors of this disease may include inheritance of susceptibilities in high and low penetrance genes. Notably, inheritance of high (e.g., HPCa1, HPCaX, BrCA1, BRCA2, CAPB, PCaP, ELAC2/HPCa2) and low penetrance susceptibility genes may account for as much as 42-50% of all PCa cases [1-8]. Common sequence variants in low penetrance genes involved in important biological pathways required for tumor progression are prevalent in sporadic PCa cases and may account for more of the public health burden. Pathways that play a role in PCa tumorigenesis include chronic inflammation, immunosuppression, and angiogenesis.

SUMMARY

The present invention is based, at least in part, on the discovery that the presence of specific allelic variants in VEGF and the VEGFR are associated with risk of developing prostate cancer (PCa). Thus, the invention includes methods for determining a subject's risk of developing PCa, based on detection of those allelic variants.

In one aspect, the invention includes methods for determining a subject's risk for developing PCa. The methods can include obtaining a sample comprising genomic DNA (gDNA) from the subject, and determining the identity, absence or presence of polymorphisms of VEGF and VEGFR as described herein. In some embodiments, the methods include obtaining a test haplotype for the subject comprising polymorphisms of VEGF and VEGFR, wherein the haplotype provides information regarding the subject's risk of developing PCa. In some embodiments, the methods further include administering a treatment to the subject to decrease their risk of developing PCa or to treat PCa. In some embodiments, the methods include surgical removal of the prostate.

Information obtained using a method described herein can be used, e.g., to select a subject population for a clinical trial, to stratify a subject population in a clinical trial, and/or to stratify subjects that respond to a treatment from those who do not respond to a treatment, or subjects that have negative side effects from those who do not.

In another aspect, the invention provides methods for selecting a subject for inclusion in a clinical trial, e.g., a trial of a treatment for PCa. The methods include obtaining a haplotype for the subject including the polymorphisms of VEGF and VEGFR described herein; determining whether the genetic profile is associated with an increased risk of developing PCa; and including the subject in the trial if the genetic profile indicates that the subject has (or does not have) an increased risk of developing PCa.

In another aspect, the invention provides methods for selecting a subject for administration of a treatment for PCa. The methods include obtaining a genetic profile for the subject, wherein the genetic profile comprises the polymorphisms of VEGF and VEGFR1 described herein; determining whether the genetic profile is associated with an increased risk of developing PCa; and administering the treatment to the subject if the genetic profile indicates that the subject has an increased risk of developing PCa.

In another aspect, the invention provides methods for selecting a treatment for administration to a subject. The methods include obtaining a genetic profile for the subject, wherein the genetic profile the polymorphisms of VEGF and VEGFR1 described herein; determining whether the genetic profile is associated with an increased risk of developing PCa; and administering the treatment for PCa to the subject if the genetic profile indicates that the subject has an increased risk of developing PCa.

In some embodiments of the methods described herein, the subject is a male of African descent.

In some embodiments, the methods described herein include determining the identity of alleles at VEGF 2482 (rs3025040) and VEGFR IVS6+54 (rs7692791). Specifically, the presence of VEGF 2482 C>T and VEGFR IVS6+54 G>A variants is associated with an increased risk of developing PCa.

Also provided herein are kits for use in detection of genetic profiles associated with PCa, including at least one nucleic acid probe that hybridizes to a sequence that includes a polymorphism described herein, or can be used to amplify a sequence that includes a polymorphism described herein.

Also provided are arrays that include a substrate having a plurality of addressable areas, wherein one or more of the addressable areas includes one or more probes that can be used to detect a polymorphism described herein.

As used herein, a "genetic profile" is one or a set of signature genetic changes (e.g., polymorphisms). A "genetic profile" as used herein is information regarding the presence or absence of one or more genetic markers in a subject. A genetic profile can consist of a variety of genetic markers, including indels (insertions or deletions of the DNA at particular locations on the chromosome); single nucleotide polymorphisms (SNPs) in which a particular nucleotide is changed; microsatellites; and minisatellites. A "haplotype" is one or a set of signature genetic changes (i.e., a genetic profile) that includes markers that are normally grouped closely together on the DNA strand, and are usually inherited as a group;

"Linkage disequilibrium" refers to when the observed frequencies of haplotypes in a population does not agree with haplotype frequencies predicted by multiplying together the frequency of individual genetic markers in each haplotype.

The term "chromosome" as used herein refers to a gene carrier of a cell that is derived from chromatin and comprises DNA and protein components (e.g., histones). The conventional and internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that encodes a gene product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intra-specific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or genetic profiles described herein. The stratification can be performed, e.g., in the course of analysis, or can be used in creation of distinct groups or in other ways.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 is a list of the sequences associated with the allelic variants described herein.

FIG. 3 is a list of exemplary primers and probes useful in the methods described herein.

DETAILED DESCRIPTION

Figure 1:
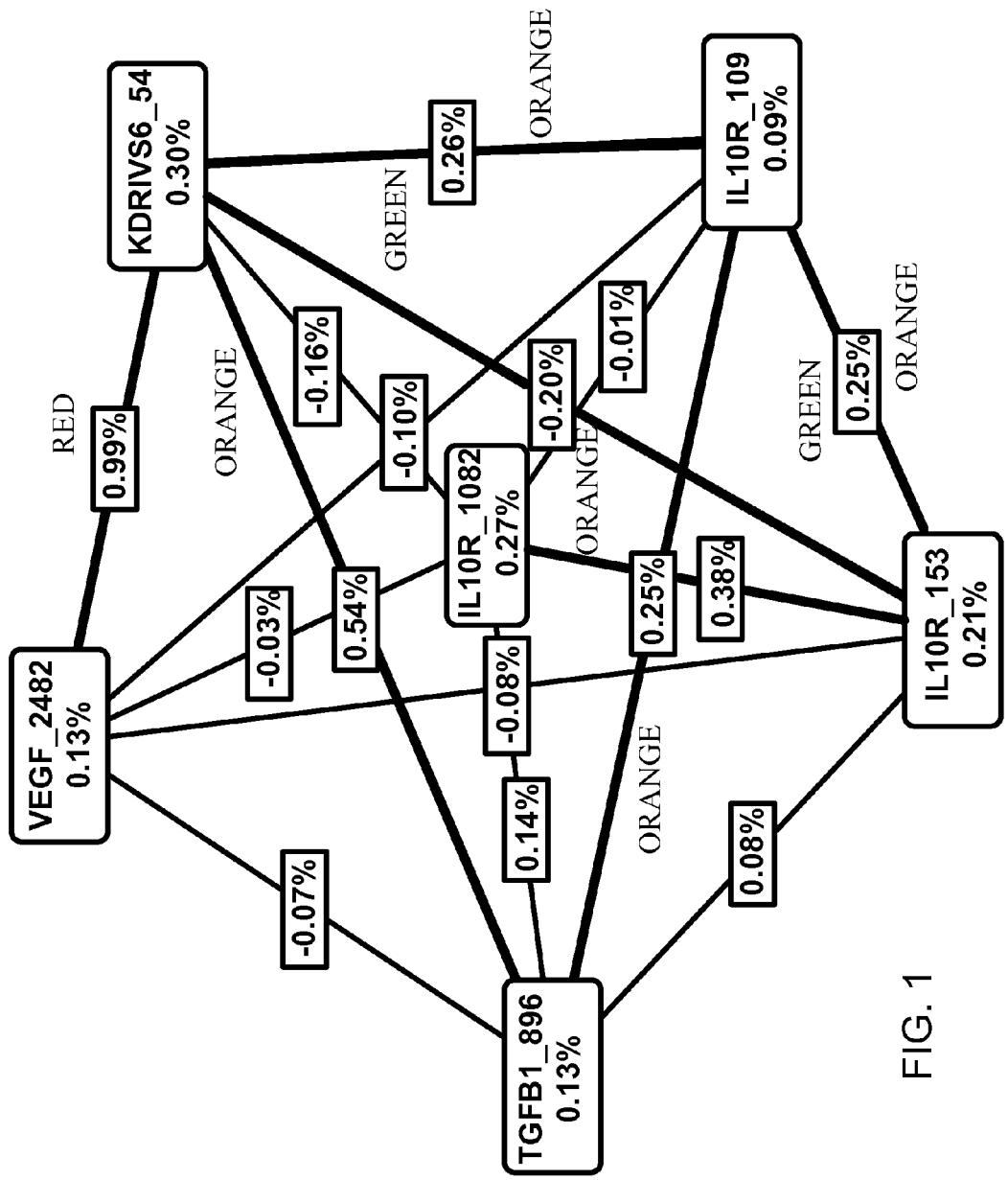
FIG. 1 is a schematic illustration of an interaction entropy model, which describes the percent entropy that is explained by each Angiogenesis-Related SNP or a combination of two loci within the study population.

Prostate cancer (PCa) incidence and mortality are disproportionately high among African-American (AA) men. Its detection and perhaps its disparities could be improved through the identification of genetic susceptibility biomarkers within essential biological pathways. Interactions among highly variant genes, central to angiogenesis, may modulate susceptibility for prostate cancer, as previous demonstrated. This study evaluates the interplay among three highly variant genes (i.e., IL-10, TGFβR-1, VEGF), their receptors and their influence on PCa within a case-control study consisting of an under-served population.

The study described herein evaluated single gene and joint modifying effects on PCa risk in a case-control study comprised of 855 AA men (196 cases and 659 controls) using TaqMan qPCR. Interaction among polymorphic IL-10, TGFβ-1 and VEGF was analyzed using conventional logistic regression analysis (LR) models, multi-dimensionality reduction (MDR) and interaction entropy graphs. Symbolic modeling allowed validation of gene-gene interaction findings identified by MDR.

As shown herein, no significant single gene effects were demonstrated in relation to PCa risk. However, carriers of the VEGF 2482T allele had a three-fold increase in the risk of developing aggressive PCa. The presence of VEGF 2482T combined with VEGFR IVS6+54 loci were highly significant for the risk of PCa based on MDR and symbolic modeling analyses. These findings were substantiated by 1000-fold cross validation permutation testing (P=0.04), respectively.

These findings suggest the inheritance of VEGF and VEGFR IVS6+54 sequence variants may jointly modify PCa susceptibility through their influence on angiogenesis. Therefore, the detection of these variants can be used to identify subjects with an increased risk of developing PCa.

The VEGF C>T change at position 2482 results in the loss of an important repressor element silencing transcription factor (REST/NRSF). Based on previously published studies (48, 49) in silico analysis (50), the loss of the "C" allele may result in the loss of a REST/NRSF binding site. This would result in diminished capacity to repress VEGF transcription. It has also been suggested that disregulated VEGF contributes to tumor progression through enhanced angiogenesis (51, 52). Similarly, the VEGFR A to G change at position IVS6+54 results in the gain of a CCAAT/enhancer binding protein (C/EBP) site (50). The presence of a C/EBP site would enable leucine-zipper transcription factors to bind and promote the transcription of VEGFR (50, 53). There is emerging evidence that a C/EBPβ protein isoforms (i.e., LIP) disrupt normal growth, development and tumorigenesis. Interestingly, neither of the aforementioned SNPs alone significantly modified PCa risk; however, both MDR and symbolic modeling revealed a complex interaction between these two markers may contribute to PCa risk.

Methods of Diagnoses and Evaluation of Risk

Described herein are a variety of methods for the diagnosis of susceptibility to PCa. "Susceptibility" does not necessarily mean that the subject will develop PCa, but rather that the subject is, in a statistical sense, more likely to develop PCa than a member of the general population, i.e., has an increased risk of developing PCa. As used herein, susceptibility to PCa exists if the subject has a genetic profile associated with an increased risk of PCa as described herein. Ascertaining whether the subject has such a genetic profile is included in the concept of diagnosing susceptibility to PCa as used herein. Such determination is useful, for example, for purposes of diagnosis, treatment selection, and genetic counseling. Thus, the methods described herein can include obtaining a genetic profile associated with an increased risk of PCa as described herein for the subject.

As used herein, "obtaining a genetic profile" includes obtaining information regarding the identity, presence or absence of one or more genetic markers in a subject. Obtaining a genetic profile can, but need not, include obtaining a sample comprising DNA from a subject, and/or assessing the identity, presence or absence of one or more genetic markers in the sample. The individual or organization who obtains the genetic profile need not actually carry out the physical analysis of a sample from a subject; the genetic profile can include information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Obtaining a genetic profile can also include or consist of reviewing a subject's medical history, where the medical history includes information regarding the identity, presence or absence of one or more genetic markers in the subject, e.g., results of a genetic test.

In some embodiments, to detect the presence of a genetic profile described herein, a biological sample that includes nucleated cells (such as blood, a cheek swab or mouthwash) is prepared and analyzed for the presence or absence of pre-selected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for PCa if the subject has an increased risk of developing PCa. As another example, a drug or treatment may be indicated for individuals with a certain genetic profile, and the insurance company would only reimburse the health care provider (or the insured individual) for prescription or purchase of the drug if the insured individual has that genetic profile. The presence or absence of the genetic profile in a patient may be ascertained by using any of the methods described herein.

Information gleaned from the methods described herein can also be used to select or stratify subjects for a clinical trial. For example, the presence of a selected genetic profile described herein can be used to select a subject for a trial. The information can optionally be correlated with clinical information about the subject, e.g., diagnostic or endophenotypic information.

Genetic Profiles Associated with PCa

As described herein, genetic profiles associated with PCa include SNPs at VEGF 2482 combined with VEGFR1 IVS6+54. Specifically, the presence of at least one VEGF 2482 T allele combined with at least one VEGFR1 IVS6+54 G allele, is associated with an increased risk of developing PCa.

Linkage Disequilibrium Analysis

Linkage disequilibrium (LD) is a measure of the degree of association between alleles in a population. One of skill in the art will appreciate that genetic profiles involving markers within 1 Linkage Disequilibrium Unit (LDU) of the polymorphisms described herein can also be used in a similar manner to those described herein. LDUs share an inverse relationship with LD so that regions with high LD (such as haplotype blocks) have few LDUs and low recombination, whilst regions with many LDUs have low LD and high recombination. Methods of calculating LDUs are known in the art (see, e.g., Morton et al., Proc Natl Acad Sci USA 98(9):5217-21 (2001); Tapper et al., Proc Natl Acad Sci USA 102(33): 11835-11839 (2005); Maniatis et al., Proc Natl Acad Sci USA 99:2228-2233 (2002)).

Thus, in some embodiments, the methods include analysis of polymorphisms that are within 1 LDU of a polymorphism described herein. Methods are known in the art for identifying such polymorphisms; for example, the International HapMap Project provides a public database that can be used, see hapmap.org, as well as The International HapMap Consortium, Nature 426:789-796 (2003), and The International HapMap Consortium, Nature 437:1299-1320 (2005). Generally, it will be desirable to use a HapMap constructed using data from individuals who share ethnicity with the subject, e.g., a HapMap for African-Americans would ideally be used to identify markers within 1 LDU of a marker described herein for use in genotyping a subject of African American descent.

Alternatively, methods described herein can include analysis of polymorphisms that are within a value defined by Lewontin's D' (linkage disequilibrium parameter, see Lewontin, Genetics 49:49-67 (1964)) of a polymorphism described herein. Results can be obtained, e.g., from on line public resources such as HapMap.org. The simple linkage disequilibrium parameter (D) reflects the degree to which alleles at two loci (for example two SNPs) occur together more often (positive values) or less often (negative values) than expected in a population as determined by the products of their respective allele frequencies. For any two loci, D can vary in value from −0.25 to +0.25. However, the magnitude of D (Dmax) varies as function of allele frequencies. To control for this, Lewontin introduced the D' parameter, which is D/Dmax and varies in value from −1 (alleles never observed together) to +1 (alleles always observed together). Typically, the absolute value of D' (i.e., |D'|) is reported in online databases, because it follows mathematically that positive association for one set of alleles at two loci corresponds to a negative association of equal magnitude for the reciprocal set. This disequilibrium parameter varies from 0 (no association of alleles at the two loci) to 1 (maximal possible association of alleles at the two loci).

Thus, in some embodiments, the methods include analysis of polymorphisms that are within D'>0.75, or D'=1, for pairwise comparisons, of a polymorphism described herein.

Methods of Determining the Presence or Absence of a Genetic Profile Associated with Risk of Developing PCa The methods described herein include determining the presence or absence of genetic profiles associated with PCa. In some embodiments, an association with PCa is determined by the presence of a shared genetic profile between the subject and an affected reference individual, e.g., a first or second-degree relation of the subject, and the absence of the genetic profile in an unaffected reference individual. Thus the methods can include obtaining and analyzing a sample from a suitable reference individual.

Samples that are suitable for use in the methods described herein contain genetic material, e.g., genomic DNA (gDNA). Non-limiting examples of sources of samples include urine, blood, and tissue. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

The absence or presence of a genetic profile associated with PCa as described herein can be determined using methods known in the art, e.g., gel electrophoresis, capillary electrophoresis, size exclusion chromatography, sequencing, and/or arrays to detect the presence or absence of the marker(s) of the genetic profile. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see *Current Protocols in Molecular Biology*, Ausubel, F. et al., eds., John Wiley & Sons 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

Other methods include direct manual sequencing (Church and Gilbert, Proc. Natl. Acad. Sci. USA 81:1991-1995 (1988); Sanger et al., Proc. Natl. Acad. Sci. 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)), mobility shift analysis (Orita et al., Proc. Natl. Acad. Sci. USA 86:2766-2770 (1989)), restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach and Dveksler, (Eds.); McPherson et al., *PCR Basics: From Background to Bench* (Springer Verlag, 2000); Mattila et al., Nucleic Acids Res., 19:4967 (1991); Eckert et al., *PCR Methods and Applications*, 1:17 (1991); *PCR* (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a genetic profile as described herein. The genetic profile can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)-glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of PCa.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to PCa.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., Nature (London) 324:163-166 (1986)). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for particular a polymorphism can be prepared using standard methods (see Ausubel et al., *Current Protocols in Molecular Biology*, supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to PCa) to DNA from the subject is indicative of susceptibility to PCa.

In some embodiments, fluorescence polarization template-directed dye-terminator incorporation (FP-TDI) is used to determine which of multiple polymorphic variants of a polymorphism is present in a subject (Chen et al., (1999) Genome Research, 9(5):492-498). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., (2000) Genome Research, 10(8): 1249-1258). Additional methods include, for example, PCR amplification in combination with denaturing high performance liquid chromatography (dHPLC) (Underhill, P. A., et al., Genome Research, Vol. 7, No. 10, pp. 996-1005, 1997).

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence. The probe sequence must also be sufficiently long so that the probe exhibits selectivity for the target sequence over non-target sequences. For example, the probe will be at least 20, e.g., 25, 30, 35, 50, 100, 200, 300, 400, 500, 600, 700, 800, 900 or more, nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., polymorphisms as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem., 1998, 73(1):6-22, Wheeless et al., Cytometry 1994, 17:319-326, and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethyl-rhodamine-5-(and-6)-isothiocyanate, 5-(and-6)-carboxytet-ramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a,4a diaza-3-indacenepro-pionic acid, eosin-5-isothiocyanate, erythrosin-5-isothiocy-anate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Arrays and Uses Thereof

In another aspect, the invention features arrays that include a substrate having a plurality of addressable areas, and methods of using them. At least one area of the plurality includes a nucleic acid probe that binds specifically to a sequence comprising a polymorphism described herein, and can be used to detect the absence or presence of said polymorphism, e.g., one or more SNPs, microsatellites, minisatellites, or indels, as described herein, to determine a genetic profile. For example, the array can include one or more nucleic acid probes that can be used to detect a polymorphism listed in Table 1, e.g., at VEGFR IVS6+54 and/or VEGF 2482. In some embodiments, the array further includes at least one area that includes a nucleic acid probe that can be used to specifically detect another marker associated with PCa, as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 4p and/or 22q, e.g., a region between SNP rs801720 and SNP rs710123, e.g., a region between SNP rs713692 and rs756638, optionally, a different portion of genomic DNA, e.g., a portion that includes a different portion of human chromosomes 22 and/or 4, or another chromosome, e.g., including another region associated with PCa., and detecting binding of a nucleic acid from the sample to the array. Optionally, the method includes amplifying nucleic acid from the sample, e.g., genomic DNA that includes a portion of a human chromosome described herein, and, optionally, a region that includes another region associated with PCa, prior to or during contact with the array.

In some aspects, the methods described herein can include using an array that can ascertain differential expression patterns or copy numbers of one or more genes in samples from normal and affected individuals (see, e.g., Redon et al., Nature. 444(7118):444-54 (2006)). For example, arrays of probes to a marker described herein can be used to measure polymorphisms between DNA from a subject having PCa, and control DNA, e.g., DNA obtained from an individual that does not have PCa, and has no risk factors for PCa. Since the clones on the array contain sequence tags, their positions on the array are accurately known relative to the genomic sequence. Different hybridization patterns between DNA from an individual afflicted with PCa and DNA from a normal individual at areas in the array corresponding to markers in human chromosome 4p and/or 22q as described herein, and, optionally, one or more other regions associated with PCa, are indicative of a risk of PCa. Methods for array production, hybridization, and analysis are described, e.g., in Snijders et al., (2001) *Nat. Genetics* 29:263-264; Klein et al., (1999) Proc. Natl. Acad. Sci. U.S.A. 96:4494-4499; Albertson et al., (2003) Breast Cancer Research and Treatment 78:289-298; and Snijders et al. "BAC microarray based comparative genomic hybridization." In: Zhao et al. (eds), *Bacterial Artificial Chromosomes: Methods and Protocols*, Methods in Molecular Biology, Humana Press, 2002. Real time quantitative PCR can also be used to determine copy number.

In another aspect, the invention features methods of determining the absence or presence of a genetic profile associated with PCa as described herein, using an array described above. The methods include providing a two dimensional array having a plurality of addresses, each address of the plurality being positionally distinguishable from each other address of the plurality having a unique nucleic acid capture probe, contacting the array with a first sample from a test subject who is suspected of having or being at risk for PCa, and comparing the binding of the first sample with one or more references, e.g., binding of a sample from a subject who is known to have PCa, and/or binding of a sample from a subject who is unaffected, e.g., a control sample from a subject who neither has, nor has any risk factors for PCa. In some embodiments, the methods include contacting the array with a second sample from a subject who has PCa; and comparing the binding of the first sample with the binding of the second sample. In some embodiments, the methods include contacting the array with a third sample from a cell or subject that does not have PCa and is not at risk for PCa; and comparing the binding of the first sample with the binding of the third sample. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Prostate Cancer (PCa)

PCa is an uncontrolled (malignant) growth of cells in the prostate gland which is located at the base of the urinary bladder and is responsible for helping control urination as well as forming part of the semen. Prostate cancer is the second leading cause of death of males in the U.S. The methods described herein can be used to determine an individual's risk of developing PCa.

A number of risk factors for PCa are known in the art, including age (increased over 40, more increased over 50, highest over 65); race/ethnicity (highest in men of African descent, e.g., African American men, lower in Asian and Latino/Hispanic men); nationality (highest in North America, northwestern Europe, Australia, and Carribean, lower in Asia, Africa, Central America, and South America); family history; diet (consumption of a lot od red meat and/or high-fat dairy products increases risk); obesity (BMI>29); lack of exercise; inflammation of the prostate; infection (e.g., sexually transmitted diseases); vasectomy; and other genes (e.g., HPCa1, HPCaX, BrCA1, BRCA2, CAPB, PCaP, ELAC2/HPCa2) or genetic variants associated with increased risk of PCa (1-8).

In particular, the methods described herein are useful for determining risk of developing PCa in men of African descent, e.g., West African descent. In the US alone, nearly 31,000 cases of prostate cancer were diagnosed in African American men in 2007, which accounted for 37% of all cancers diagnosed in African American men. Despite recent improvement in treatments, PCa incidence and mortality remain higher among African American men that their white counterparts. See Odedina et al., Infect. Agents Can. 4(Suppl 1):S2 (pp. 1-8) (2009).

Current Treatment of PCa

Four treatment options are presently the standard of care: Watchful waiting (closely monitoring the subject's condition without giving any treatment until symptoms appear or change, usually used in older men with other medical problems and early-stage disease); surgery (radical prostatectomy, lymphadenectomy, transurethral resection of the prostate (TURP); orchiectomy); radiation therapy (external or internal); and hormone therapy (e.g., with LHRH agonists, anti-androgens, and estrogens). In addition, a number of experimental treatments are being evaluated in clinical trials, such as cryosurgery, chemotherapy, high-intensity focused ultrasound, and biologic therapy (e.g., using PCa-specific antibodies).

Methods of Determining Treatment Regimens and Methods of Treating PCa

As described herein, the presence of genetic profiles described herein has been correlated with an increased risk of developing or having PCa. Thus, the new methods can also include selecting a treatment regimen for a subject determined to be at risk for developing PCa, based upon the absence or presence of a genetic profile associated with PCa as described herein. The determination of a treatment regimen can also be based upon the absence or presence of other risk factors associated with PCa, e.g., as described herein. Therefore, the methods of the invention can include selecting a treatment regimen for a subject having one or more risk factors for PCa, and having a genetic profile described herein. The methods can also include administering a treatment regimen to a subject having, or at risk for developing, PCa to thereby treat, prevent or delay further progression of the disease. A treatment regimen can include the administration of antipsychotic medications to a subject identified as at risk of developing PCa before the onset of any psychotic episodes.

As used herein, the term "treat" or "treatment" is defined as the application or administration of a treatment regimen, e.g., a therapeutic agent or modality, to a subject, e.g., a patient. The subject can be a patient having PCa, a symptom of PCa or at risk of developing (i.e., having one or more of the risk factors for PCa known in the art or described herein) PCa. The treatment can be to cure, heal, alleviate, relieve, alter, remedy, ameliorate, palliate, improve or affect PCa, the symptoms of PCa or the predisposition toward PCa.

The methods of the invention, e.g., methods of determining a treatment regimen and methods of treatment or prevention of PCa, can further include the step of monitoring the subject, e.g., for a change (e.g., an increase or decrease) in one or more of the diagnostic criteria for PCa listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. In a preferred embodiment, a treatment for PCa can be evaluated by administering the same treatment or combinations or treatments to a subject having PCa and a genetic profile as described herein and to a subject that has PCa but does not have a genetic profile as described herein. The effects of the treatment or combination of treatments on each of these subjects can be used to determine if a treatment or combination of treatments is particularly effective on a sub-group of subjects having PCa. In other embodiments, various treatments or combinations of treatments can be evaluated by administering two different treatments or combinations of treatments to at least two different subjects having PCa and a genetic profile as described herein. Such methods can be used to determine if a particular treatment or combination of treatments is more effective than others in treating this subset of PCa patients.

Various treatment regimens are known for treating PCa, e.g., as described herein.

Pharmacogenomics

With regards to both prophylactic and therapeutic methods of treatment of PCa, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market, as detailed previously (e.g., Eichelbaum et al., Clin. Exp. Pharmacol. Physiol. 23:983-985 (1996) and Linder et al., Clin. Chem. 43:254-266 (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype. For example, if a subject is determined to have a genetic profile associated with increased risk of developing PCa as described herein that includes risk alleles in VEGF and VEGFR, a therapeutic treatment that blocks VEGF signaling, e.g., a VEGF or VEGF inhibitor, can be administered.

There are at least three methods to block VEGF signaling that have been used to date. The first method is to inhibit VEGF (e.g. VEGF-A, -B, -C, -D, PGF) and/or VEGFR (e.g. VEGFR-1, -2, -3) using antibodies. Examples include: Avastin (bevacizumab), a recombinant humanized monoclonal antibody that binds to VEGF-A and prevents the interaction of VEGF-A to its receptors (e.g., VEGFR-1 and VEGFR-2 as described previously, see, e.g., Presta et al., (1997). Cancer Res. 57: 4593-4599; Hurwitz et al., (2004). N. Engl. J. Med. 350:2335-2342); 2C3, a mouse monoclonal antibody against VEGF-A (Zhang et al., (2002). Angiogenesis. 5:35-44; Brekken et al., (1998) Cancer Res. 58: 1952-9); IMC-1121B, a human monoclonal antibody against VEGFR-2 (Rockwell and Goldstein, U.S. Pat. No. 6,811,779); CDP-791, PEGylated, humanized di-Fab fragment that binds to VEGFR-2 (Ton et al., (2007) Clin. Cancer Res. 13:7113-711). Lucentis (ranibizumab) is a recombinant humanized monoclonal antibody that binds to VEGF-A, but its approved usage is for treatment of patients with neovascular age-related macular degeneration (available from Genentech).

A second method uses protein kinase inhibitors to inhibit VEGFR (e.g. VEGFR-1, -2, -3). At least two known FDA-approved small molecule inhibitors are on the market: Sutent (sunitinib) (Goodman et al., Clin. Cancer Res. 13:1367-1373 (2007)) and Nexavar (sorafenib) (Kane et al., Clin. Cancer Res. 12:7271-8 (2006)). Other kinase inhibitors include, but are not limited to: Vatalanib (PTK787/ZK222584) which inhibits VEGFR-1, -2, and -3 (Wood et al., Cancer Res. 60:2178-2189 (2000)); CEP-7055, inhibitor of VEGFR-1, -2, and -3 (Ruggeri et al., Cancer Res. 63: 5978-5991 (2003)); CP-547,632, inhibitor of VEGFR-2 and FGF (Beebe et al., Cancer Res. 63: 7301-7309 (2003)).

A third method uses the so-called "VEGF-trap," i.e., soluble hybrid VEGF receptors that bind to the VEGF ligand and prevent binding to VEGFRs (Holash et al., Proc. Natl. Acad. Sci. 99:11393-11398 (2002)).

In some embodiments, the anti-angiogenic agent is an anti-Vascular Endothelial Growth Factor (VEGF) agent, e.g., an anti-VEGF antibody or antigen-binding portions thereof (such as Fv, Fab, or scFv portions) to inhibit VEGF binding to KDR and/or flt receptors, e.g., Avastin® (Bevacizumab). Avastin is a recombinant humanized monoclonal IgG1 antibody that binds to and inhibits the biologic activity of human VEGF both in vitro and in vivo. Bevacizumab contains human framework regions and the complementary-determining regions of a murine antibody that binds to VEGF (Presta et al., "Humanization of an anti-vascular endothelial growth factor monoclonal antibody for the therapy of solid tumors and other disorders." Cancer Res 1997; 57:4593-9). Avastin is available from Genentech (South San Francisco, Calif.). See also: Schlaeppi and Wood, "Targeting Vascular Endothelial Growth Factor (VEGF) for Anti-Tumor Therapy, by Anti-VEGF Neutralizing Monoclonal Antibodies or by VEGF Receptor Tyrosine-Kinase Inhibitors," Cancer and Metastasis Rev. 1999; 18:473-481; U.S. Pat. Nos. 7,169,901; 7,056,509; and 7,297,334; U.S. Pat. Pub. No. 20020032315; 20080187966; and 20090010883; and PCT No. WO 94/10202. In some embodiments, the antibody binds specifically to VEGF and block binding to VEGFR1, to VEGFR2, or block binding to both VEGFR1 and VEGFR2.

Other anti-VEGF agents include VEGF antagonists, which could compete with VEGF for binding to KDR and/or flt receptors (e.g. soluble truncated forms of flt receptor, which bind to VEGF, as described, for example, in WO 94/21679); and tyrosine kinase inhibitors.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing PCa.

In one embodiment, a physician or clinician may consider applying knowledge obtained in relevant pharmacogenomics studies, e.g., using a method described herein, when determining whether to administer a pharmaceutical composition, e.g., an antipsychotic agent or a combination of antipsychotic agents, to a subject. In another embodiment, a physician or clinician may consider applying such knowledge when determining the dosage, e.g., amount per treatment or frequency of treatments, of a treatment, e.g., a antipsychotic agent or combination of antipsychotic agents, administered to a patient.

As one example, a physician or clinician may determine (or have determined, e.g., by a laboratory) the genetic profile of a subject as described herein, and optionally one or more other markers associated with PCa, of one or a group of subjects who may be participating in a prostate cancer clinical trial designed to test the efficacy of a pharmaceutical composition, e.g., an antipsychotic or combination of antipsychotic agents, and wherein the physician or clinician attempts to correlate the genotypes of the subjects with their response to the pharmaceutical composition.

As another example, information regarding a genetic profile associated with an increased risk of PCa, as described herein, can be used to stratify or select a subject population for a clinical trial. The information can, in some embodiments, be used to stratify individuals that may exhibit a toxic response to a treatment from those that will not. In other cases, the information can be used to separate those that will be non-responders from those who will be responders. The genetic profiles described herein can be used in pharmacogenomics-based design and manage the conduct of a clinical trial, e.g., as described in U.S. Pat. Pub. No. 2003/0108938.

As another example, information regarding a genetic profile associated with an increased risk of PCa, as described herein, can be used to stratify or select human cells or cell lines for drug testing purposes. Human cells are useful for studying the effect of a polymorphism on physiological function, and for identifying and/or evaluating potential therapeutic agents for the treatment of PCa, e.g., chemotherapeutic agents. Thus the methods can include performing the present methods on genetic material from a cell line.

Theranostics

Also included herein are compositions and methods for the identification and treatment of subjects who have an increased risk of PCa, such that a theranostic approach can be taken to test such individuals to determine the effectiveness of a particular therapeutic intervention (e.g., a pharmaceutical or non-pharmaceutical intervention as described herein) and to alter the intervention to 1) reduce the risk of developing adverse outcomes and 2) enhance the effectiveness of the intervention. Thus, in addition to diagnosing or confirming the predisposition to PCa, the methods and compositions described herein also provide a means of optimizing the treatment of a subject having such a disorder. Provided herein is a theranostic approach to treating and preventing PCa, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a genetic profile as described herein and any measurable or quantifiable parameter relating to the outcome of the treatment, e.g., efficacy (the results of which may be binary (i.e., yes and no) as well as along a continuum), side-effect profile, treatment maintenance and discontinuation rates, return to work status, hospitalizations, suicidality, total healthcare cost, social functioning scales, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low suicidality, low total healthcare cost, high social function scale, favorable response to non-pharmacological treatments, and/or acceptable dose response curves) and a selected genetic profile can influence treatment such that the treatment is recommended or selected for a subject having the selected genetic profile.

Kits

Also within the scope of the invention are kits comprising a probe that hybridizes with a region of human chromosome as described herein and can be used to detect a polymorphism described herein. The kit can include one or more other elements including: instructions for use; and other reagents, e.g., a label, or an agent useful for attaching a label to the probe. Instructions for use can include instructions for diagnostic applications of the probe for assessing risk of PCa in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a labeled probe as described herein.

The kit can also include one or more additional probes that hybridize to and detect other genetic variants associated with risk for PCa, e.g., as known in the art and described herein. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Databases

Also provided herein are databases that include a list of polymorphisms as described herein, and wherein the list is largely or entirely limited to polymorphisms identified as useful in performing genetic diagnosis of or determination of susceptibility to PCa as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular genetic profile and the information regarding the subject, e.g., to detect correlations between a genetic profile and a particular endophenotype, or treatment response.

Engineered Cells

Also provided herein are engineered cells that harbor one or more polymorphism described herein, e.g., one or more polymorphisms that constitute a genetic profile associated with PCa. Such cells are useful for studying the effect of a polymorphism on physiological function, and for identifying and/or evaluating potential therapeutic agents for the treatment of PCa, e.g., anti-psychotics.

As one example, includes cells harboring one or more of the variant angiogenesis-associated alleles described herein Methods are known in the art for generating cells possessing altered sequence variants, such as homologous recombination between the endogenous gene and exogenous DNA molecule that is introduced into a cell (e.g., a cell of an animal). In some embodiments, the cells can be used to generate transgenic animals using well established methods.

The cells are preferably mammalian cells, e.g., neuronal type cells, in which an endogenous gene has been altered to include a polymorphism as described herein. Techniques such as targeted homologous recombination, can be used to insert the heterologous DNA, e.g., as described in Chappel, U.S. Pat. No. 5,272,071; and WO 91/06667.

EXAMPLES

The invention is further described in the following examples, which do not limit the scope of the invention described in the claims.

Example 1

To further clarify the impact of sequence variants detected in IL-10, TGFβ1, VEGF and their corresponding receptors in relation to PCa, the current study evaluated the individual and joint modifying effects of 15 sequence variants in relation to PCa risk among 855 African-Americans. Based on their role in angiogenesis, it was hypothesized that inheritance of IL-10 low-expressing, TGFβ1 high-expressing and VEGF high-expressing alleles would increase the risk of PCa and high tumor grade, than compared to the other alleles. These SNPs were chosen, in part, based on their capacity to alter protein/mRNA expression or signaling pathways in relationship with cancer outcomes or other malignancies (Table 1).

ing program. PCa patients (n=193) and controls (n=666), ages 26-91, were recruited between years 2001 and 2005. Participants were selected based on their willingness to have a blood sample drawn for future genetic epidemiology. PCa ages 41-91 (median=65), was diagnosed by an urologist, due to elevated prostate specific antigen (PSA>2.0 ng/ml), abnormal digital rectal examination (DRE), and/or unfavorable histological findings following biopsy. Clinical characteristics including Gleason score, PSA, and age at diagnosis for the study participants were obtained from medical records, as detailed in Table 2. Tumor grade was collected for 58.0% of the cases (n=112). Histopathological grade was recorded as the Gleason score. Specifically histological grades I/II and III were equivalent to Gleason scores 1-4, 5-7 and 8-10, respec-

TABLE 1

Functional Consequences of Selected SNPs in the Angiogenesis Pathway and their Potential Role in Prostate Cancer Susceptibility

| Gene | rs Number | Nucleotide Change | Amino Acid Change | Impact on mRNA/Protein stability/expression | Proposed Influence on PCa risk | References |
| --- | --- | --- | --- | --- | --- | --- |
| VEGF 2482 | rs3025040 | C > T | 3' UTR | C allele may result in the loss of a REST/NRSF binding sites and diminished capacity to repress VEGF transcription | Increase | Current study |
| VEGFR IVS6+54 | rs7692791 | A > G | intronic | G results in the gain of a CCAAT/enhancer binding protein (C/EBP) site, which may enable leucine-zipper transcription factors to bind and promote the transcription of VEGFR | Increase | [30;63-65] |
| IL10 −1082 | rs1800896 | G >A | promoter | Low Expressor = AA | Increase | [30;54;55] |
| IL10 −819 | rs1800871 | C > T | promoter | Low Expressor = TT | Increase | [30;55] |
| IL10 −592 | rs1800872 | C > A | promoter | Low Expressor = AA | Increase | [30;55] |
| IL-10R −153 | rs2256111 | A > G | promoter | | | [44] |
| IL-10R Ex7-109 | rs9610 | G > A | | | | [30] |
| IL-10R Ex7 241 | rs2229113 | A > G | $R^{351}G$ | | | [30] |
| TGFB1-509 | rs1800469 | C > T | promoter | Low Expressor = CC | Decrease | [30;56-58] |
| TGFB1 896 | rs 1982073 | T > C | $Leu^{10}Pro$ | High Expressor = CC | Increase | [30;57;59] |
| TGFβR1 Ex9+195 | rs868 | A > G | 3'UTR | | Unknowm | [30;60;61] |
| VEGF −2578 | rs699947 | C > A | | High Expressor = CC | Increase | [61] |
| VEGFR +889 | rs2305948 | G > A | $V^{297}I$ | Essential for maintaining the association rate with VEGF and retention of the receptor, may alter VEGF signaling pathways | Increase | [62] |
| VEGFR+1416 | rs1870377 | T > A | $H^{472}Q$ | Essential for maintaining the association rate with VEGF and retention of the receptor; may alter VEGF signaling pathways | Increase | [62] |
| VEGFR IVS25-92 | rs1531289 | G > A | intronic | | Unknown | [62] |

Study Population and Data Management

Unrelated male residents of Washington D.C. and Columbia S.C., including 787 African-American, 4 East African, 32 West African, and 10 Afro-Caribbean subjects, were selected for this PCa case control study. Patients and healthy volunteers were recruited from the Howard University Hospital (HUH) Division of Urology PCa patient population, the HUH PCa screening program, and the South Carolina PCa screentively. Inclusion criteria of controls (n=666), ages 26-89 (median=52) were men with PSA levels less than 2.0 ng/ml and normal DREs. To minimize misclassification of controls, men who had benign prostate hyperplasia (BPH) were excluded in the current study. All subjects provided written informed consent for participation in genetic analysis under a protocol approved by the Howard University Institutional Review Board, as well as from the HUH, Division of Urology.

TABLE 2

Patient and Tumor Characteristics

| Characteristics | Cases | Controls | P-value[a] |
|---|---|---|---|
| No. of Participants, n | 193 | 666 | — |
| Age (yrs) | | | |
| Median (range) | 65 0 (41-91) | 52.0 (26-89) | <0.0001 |
| PSA in ng/ml | | | |
| Median (range) | 7.0 (0-5000) | 0.9 (0-108) | <0.0001 |
| Gleason Score n (%) | | | |
| >8 | 173 (89.6) | — | — |
| ≥8 | 20 (10.4) | — | — |
| Global West African Ancestry | | | |
| Mean (SD) | 0.73 (0.18) | 0.72 (0.16) | 0.3375 |

Abbreviations: PSA, prostate specific antigen

[a]Differences in frequencies were tested by a Chi-square test of heterogeneity (i.e., Gleason score); Differences in PSA levels between cases and controls was tested using the Wilcoxon sum Rank test for continuous variables (PSA); Variations in age and Global West African Ancestry was tested using the Anova.

Data Management

Subjects (n=62) who had 8 or more missing SNPs values across the 15 SNPs were removed from the final analysis (i.e., 27 cases and 35 controls).

Allelic Discrimination of IL-10, IL-10R, TGFβR-1, TGFβ-1, VEGF and VEGFR Sequence Variants Polymorphisms in six angiogenesis-related genes were ascertained using TaqMan Polymerase Chain Reaction (PCR) allelic discrimination assays [30]. The following fifteen alleles were detected: (1) IL-10 ($G^{-1082}A$, $C^{-819}T$, $C^{-592}A$); (2) IL-10R ($A^{-153}G$, $G^{-109}A$, $A^{241}G$); (3) TGF-β1 ($T^{896}C$, $C^{-509}T$); and (4) TGF-βR1 ($A^{195}G$); (5) VEGF ($C^{2482}T$, $C^{2582}A$); (6) VEGFR2 (IVS6 $A^{54}G$, $G^{889}A$, $T^{1416}T$, IVS25 $G^{-92}A$). The sequences for the primers and probes for IL-10 ($G^{-1082}A$) was obtained from ABI and those for, IL-10R Exon 7 ($G^{-109}A$), and TGF-βR1 (Exon 9 $A^{195}G$)] were found in the NCI SNP500 database. PrimerExpress 3.0 software (Applied Biosystems, Foster City, Calif.) was used to design allelic discrimination primer and probes for: IL-10 $C^{-819}T$, $C^{-592}A$); IL-10R ($A^{-153}G$, $A^{241}G$); VEGF ($C^{2482}T$, $C^{2582}A$); VEGFR (IVS6+$A^{54}G$, $G^{889}A$, IVS25$G^{-92}A$, and $T^{1416}A$); and TGFβ-1 ($C^{-509}T$, $T^{896}C$).

Primers for two of the SNPs are shown here; others are shown in FIG. 3.

The discrimination assay contained approximately 40 ng of germ-line DNA, 1× Universal Master Mix (Applied Biosystems), 300 nM of each primer (forward and reverse), and 100 nM of each probe (FAM and VIC) to comprise a 10 ul reaction. PCR reactions were carried out in an ABI Prism 7900HT Sequence Detection System (Applied Biosystems). The thermocycling settings consisted of two holds at 50° C. for 2 min and 95° C. for 10 min, followed by 40-42 cycles of 15 sec at 95° C., and 1 min at a specific temperature for each individual SNP. PCR reactions were completed and fluorescent intensity from the probes was measured using the ABI 7900 sequence detection system. Genotypes were assigned by SDS 2.2.1 software (Applied Biosystems). To minimize misclassification bias, laboratory technicians were blinded to the case status of subjects. To ascertain percent concordance rates, 72 samples were subjected to repeat genotyping. In order to evaluate the percent genotype contamination rate, each batch analysis (n=384) included 24 non-DNA template controls. In addition, deviations from the Hardy-Weinberg equilibrium among controls were tested using a significance level of P<0.005. All of the cases and controls were also genotyped with a set of 100 genome-wide West African ancestry (WAA) informative markers to correct for individual ancestry, as detailed previously [31]. Individuals with a West African Ancestry score of less than 25% were not considered in the final analysis.

Evaluation of Single Gene Markers Predictive of PCa Risk Using Conventional Logistic Regression.

To assess whether individuals possessing at least one variant angiogenesis-related allele have an elevated risk of developing PCa, we tested for significant differences in the distribution 15 cytokine genotypes between 196 cases and 659 controls using the chi-square test of homogeneity. Associations between PCa risk and candidate polymorphic genes, expressed as odds ratios (ORs) and corresponding 95% confidence intervals (CIs), were estimated using unconditional multivariate logistic regression (LR) models adjusted for potential confounders (age, PSA and WAA). To account for population admixture, percentage of West African Ancestry was estimated using a panel of SNP markers and included as a covariate in all LR models. All reported risk estimates and 95% CIs for the selected polymorphic genes used the following as reference genotypes: IL-10-1082 G/G, IL-10-819 C/C, IL-10-592 C/C, IL-10R-153 G/G, IL-10R-109 G/G, IL-10R

```
Rs3025040 VEGFA 2482 C/T

Forward (21nt): gcacagcaatgtcctgaagct        58.7(Tm), 48(% GC)

Reverse (26nt): Ggacagaaagacagatcacagg       59.6(Tm), 46(% GC)
                taca Probe1 (14nt): FAM- tcagagccGgtgtc- MGB      66.0(Tm), 64(% GC)

Probe2 (14nt): VIC- cagagccAgtgtcc- MGB      67.0(Tm), 64(% GC)

Rs1800469 TGFbeta1 -509 C/T

Forward (26nt): aaggagagcaattcttacaggt       59.0(Tm), 42(% GC)
                gtct Reverse (17nt): gcctccggagggtgtca            59.1(Tm), 71(% GC)

Probe1 (15nt): FAM- catccTtcaggtgtc- MGB     65.0(Tm), 53(% GC)

Probe2 (15nt): VIC- ccatccCtcaggtgt- MGB     65.0(Tm), 60(% GC)
```

241 G/G, TGFβ-1-896 T/T, TGF-β1-509 C/C, TGFβ-1R-1+195 A/A, VEGF 2482 C/C, VEGF 2578 A/A, VEGFR 889 G/G, VEGFR IVS25-92 G/G, VEGFR IVS6+54 A/A. For VEGFR 1416 the minor homozygous alleles (AA) were combined with the heterozygous (AT) genotype because of their small cell count. Test for trend included genotypes as ordinal variables. Statistical significance was assessed using a P-value <0.05. All chi-square test and LR analyses were conducted using SAS 9.1.3.

Evaluating Gene Combination Effects Using Multifactor Dimensionality Reduction.

To complement LR analyses, multifactor dimensionality reduction (MDR) was used to further evaluate gene-gene interactions associated with PCa risk. The details of MDR are detailed and reviewed elsewhere [32;33]. We used 10-fold cross-validation to estimate the average testing accuracy (ATA) and cross-validation consistency (CVC) of MDR models. The MDR model with the highest ATA and CVC was selected as the overall best model. Statistical significance was evaluated using a 1000-fold permutation test. The MDR permutation results were considered to be statistically significant at the 0.05 level. The MDR software is open-source and freely available online [34].

Interaction Graphs.

Interaction entropy was used as a third strategy to verify, visualize, and interpret combination effects identified by LR and MDR [35;36]. Interaction entropy uses information gain (IG) to gauge whether interactions between two or more variables provide more information about a class variable relative to each variable considered independently [35] and has been applied to several recent epidemiological studies [35;37-39]. The colors range from red (thickest line, marked red) representing a high degree of synergy (positive information gain), orange (thinner lines, marked orange) a lesser degree, and gold (thinnest lines, unmarked) representing independence and a midway point between synergy and redundancy. Blue represents the highest level of redundancy (negative information gain), followed by green (marked).

Validate MDR Higher Order Interaction Models Using Symbolic Modeling.

Symbolic modeling (SyMod) was used as a nonparametric and model-free approach to detect nonlinear gene-gene interactions. SyMod accepts a list of attributes (e.g. SNPs) along with a list of mathematical functions and then uses genetic programming as a stochastic search algorithm to identify an optimal model that can take any shape or form. An advantage of this approach is that it doesn't make any assumption about the functional form of the model beyond the basic mathematical functions that are provided as building blocks. A symbolic model is developed within the framework of discriminant analysis. The SyMod software has been previously described in detail by Moore and co-workers [40]. Configuration parameters included a population size of 100 models, 500 generations, a crossover rate of 0.9 and a mutation rate of 0.1.

With these settings a maximum of 50,000 models were explored. A three-way cross-validation strategy was used to prevent overfitting as described by Moore et al. [40]. Expert knowledge in the form of ReliefF scores [41] were used in a multiobjective fitness function [42] and to help guide selection [43].

Prevalence of Angiogenesis-Related Alleles Among Men of African Descent.

Fifteen SNPs were detected within 6 highly variant angiogenesis-associated genes among ~91.5-95.9% of the study participants. The genotype frequencies among controls did not deviate from the Hardy-Weinberg Equilibrium (P>0.056) with the exception of marginal departures for TGFβR1 195 (P=0.005). The reason for this deviation is unknown. Within the current study set, inheritance of at least one minor or "high-risk" (linked with reduced mRNA/protein expression) IL-10$^{-1082}$A (56.4%), IL-10$^{-819}$T (61.3%), IL-10$^{-592}$A (61.4%), IL-10RA$^{-153}$G (69.8%), IL-10R$^{-109}$G (56.7%), IL-10R$^{241}$A (35.1%), TGFβ1$^{-509}$T (38.5%), TGFβ1$^{-896}$C (62.0%), TGFβ-R1$^{+195}$G (31.6%), VEGF$^{2482}$T (27.1%), VEGF$^{2578}$C (94.5%), VEGFR$^{889}$A (40.7%), VEGFR$^{1416}$A (16.9%), VEGFR IVS25$^{-92}$A (54.4%) and VEGFR IVS6$^{+54}$A (65.7%) was fairly common among controls (Table 1, above). The genotype frequencies among controls were in agreement with the NCBI and NCI SNP500 databases [30;44].

Single gene, Haplotype and Combination Effects.

The current study evaluated the independent effects of genetic variations in highly variant cytokines in relation to PCa susceptibility using unconditional LR models. No significant main effects were observed in relation to PCa risk among our study participants (Table 3). Moreover, with the exception of VEGF C$^{2482}$T, no significant relationships were revealed in relation to disease progression. Notably, individuals who possessed two VEGF$^{2482}$C alleles had a ~3-fold increase in PCa risk (OR=3.11; 95% CI=1.23-7.89) (Table 4). The capacity of single loci as well as complex interaction models, involving two or more highly variant bases and nucleotides, were also evaluated to predict cancer risk using the MDR data-mining tool. While IL-10-1082 was the best single factor to predict PCa risk, this loci did not reach statistical significance following MDR cross-validation or 1000 fold cross validation (CVC=60%; P=0.828). There was no significant relationship between a commonly studied IL10 haplotype (ordered as −1082, −819, −592) and PCa risk. Relative to ninety-one pairwise SNP combinations, permutation testing revealed both two- and four-factor models as the best predictors of PCa. Since two- and three-factor models shared comparable outcome measures (i.e., CVC, accuracy, sensitivity, and specificity), the two factor model was selected as the overall best as well as parsimonious model. VEGF-2482 and VEGFR IVS26-54 had the highest CVC (100%) and classification accuracy (58.9%) (P-value=0.04 from permutation testing). Symbolic modeling confirmed these MDR findings with an overall accuracy of 0.5753.

TABLE 3

Association between Prostate Cancer Risk and Single Gene Effects

| Genotype | Case n (%) | Control n (%) | OR (95% CI) | Adj OR (95% CI)† | P- value†† | P- trend‡ |
|---|---|---|---|---|---|---|
| IL-10 G$^{-1082}$A | | | | | | |
| GG | 75 (39.0) | 288 (43.6) | 1.00 | 1.00 | 0.213 | 0.711 |
| GA | 95 (49.5) | 280 (42.4) | 1.30 (0.92, 1.84) | 1.40 (0.86, 2.29) | | |
| AA | 22 (11.5) | 92 (14.0) | 0.92 (0.54, 1.56) | 1.36 (0.68, 2.69) | | |
| GA + AA | 117 (61.0) | 372 (56.4) | 1.21 (0.87, 1.68) | 1.39 (0.88, 2.21) | | |

TABLE 3-continued

Association between Prostate Cancer Risk and Single Gene Effects

| Genotype | Case n (%) | Control n (%) | OR (95% CI) | Adj OR (95% CI)† | P-value†† | P-trend‡ |
|---|---|---|---|---|---|---|
| IL-10C$^{-819}$T | | | | | | |
| CC | 76 (39.8) | 246 (38.7) | 1.00 | 1.00 | 0.848 | 0.633 |
| TC | 85 (44.5) | 278 (43.8) | 0.99 (0.70, 1.41) | 0.98 (0.61, 1.56) | | |
| TT | 30 (15.7) | 111 (17.5) | 0.88 (0.54, 1.41) | 0.58 (0.29, 1.13) | | |
| TC + TT | 115 (60.2) | 389 (61.3) | 0.96 (0.69 1.33) | 0.85 (0.55, 1.32) | | |
| IL-10C$^{-592}$A | | | | | | |
| CC | 72 (38.1) | 251 (38.6) | 1.00 | 1.00 | 0.875 | 0.882 |
| CA | 87 (46.0) | 288 (44.2) | 1.05 (0.74, 1.50) | 1.04 (0.65, 1.65) | | |
| AA | 30 (15.9) | 122 (17.2) | 0.93 (0.58, 1.51) | 0.53 (0.27, 1.07) | | |
| CA + AA | 117 (61.9) | 400 (61.4) | 1.02 (0.73, 1.42) | 0.88 (0.57, 1.37) | | |
| IL-10R A$^{-153}$G | | | | | | |
| AA | 63 (32.8) | 199 (30.2) | 1.00 | 1.00 | 0.253 | 0.162 |
| AG | 95 (49.5) | 307 (46.5) | 0.98 (0.68, 1.41) | 1.20 (0.71, 2.01) | | |
| GG | 34 (17.7) | 154 (23.3) | 0.70 (0.44, 1.11) | 1.01 (0.53, 1.92) | | |
| AG + GG | 129 (67.2) | 461 (69.8) | 0.88 (0.63, 1.25) | 1.14 (0.70, 1.85) | | |
| IL-10R G$^{-109}$A | | | | | | |
| AA | 78 (41.0) | 283 (43.3) | 1.00 | 1.00 | 0.599 | 0.930 |
| GA | 90 (47.4) | 284 (43.4) | 1.15 (0.81, 1.62) | 0.92 (0.57, 1.48) | | |
| GG | 22 (11.6) | 87 (13.3) | 0.92 (0.54, 1.56) | 0.58 (0.27, 1.24) | | |
| GA + AA | 112 (59.0) | 371 (56.7) | 1.10 (0.79, 1.52) | 0.83 (0.53, 1.31) | | |
| IL-10R G$^{241}$A | | | | | | |
| GG | 125 (66.1) | 427 (64.9) | 1.00 | 1.00 | 0.705 | 0.575 |
| AG | 58 (30.7) | 201 (30.5) | 0.99 (0.69, 1.40) | 0.82 (0.51, 1.32) | | |
| AA | 6 (3.2) | 30 (4.6) | 0.68 (0.28, 1.68) | 0.41 (0.11, 1.48) | | |
| AG + AA | 64 (33.9) | 231 (35.1) | 0.95 (0.67, 1.33) | 0.76 (0.48, 1.21) | | |
| TGFB1 C$^{-509}$T | | | | | | |
| CC | 114 (60.3) | 398 (61.5) | 1.00 | 1.00 | 0.297 | 0.398 |
| CT | 59 (31.2) | 214 (33.1) | 0.96 (0.68, 1.37) | 1.05 (0.66, 1.69) | | |
| TT | 16 (8.5) | 35 (5.4) | 1.60 (0.85, 2.99) | 1.94 (0.82, 4.58) | | |
| CT + TT | 75 (39.7) | 249 (38.5) | 1.05 (0.76, 1.46) | 1.16 (0.75, 1.81) | | |
| TGFB1 T$^{-896}$C | | | | | | |
| TT | 62 (33.3) | 244 (38.0) | 1.00 | 1.00 | 0.516 | 0.338 |
| CT | 84 (45.2) | 269 (41.8) | 1.23 (0.85, 1.78) | 1.11 (0.67, 1.86) | | |
| CC | 40 (21.5) | 130 (20.2) | 1.21 (0.77, 1.90) | 1.22 (0.66, 2.27) | | |
| CT + CC | 124 (66.7) | 399 (62.0) | 1.22 (0.87, 1.72) | 1.15 (0.72, 1.84) | | |
| TGFB-R1 A$^{-195}$G | | | | | | |
| AA | 141 (73.4) | 443 (68.4) | 1.00 | 1.00 | 0.400 | 0.233 |
| GA | 43 (22.4) | 175 (27.0) | 0.77 (0.53, 1.13) | 0.78 (0.47, 1.28) | | |
| GG | 8 (4.2) | 30 (4.6) | 0.84 (0.38, 1.87) | 0.79 (0.24, 2.54) | | |
| GA + GG | 51 (26.6) | 205 (31.6) | 0.78 (0.54, 1.12) | 0.78 (0.48, 1.26) | | |
| VEGF C$^{2482}$T | | | | | | |
| CC | 148 (77.5) | 480 (72.9) | 1.00 | 1.00 | 0.331 | 0.154 |
| CT | 41 (21.5) | 163 (24.8) | 0.82 (0.55, 1.20) | 0.78 (0.45, 1.34) | | |
| TT | 2 (1.0) | 15 (2.3) | 0.43 (0.10, 1.91) | 0.72 (0.12, 4.30) | | |
| CC + TT | 46 (22.5) | 178 (27.1) | 0.78 (0.54, 1.15) | 0.77 (0.46, 1.31) | | |
| VEGF C$^{2578}$A | | | | | | |
| AA | 12 (6.3) | 35 (5.5) | 1.00 | 1.00 | 0.662 | 0.734 |
| CA | 53 (27.9) | 198 (31.2) | 0.78 (0.38, 1.61) | 0.99 (0.34, 2.88) | | |
| CC | 125 (65.8) | 402 (63.3) | 0.91 (0.46, 1.80) | 1.44 (0.52, 3.99) | | |
| CA + CC | 178 (93.7) | 600 (94.5) | 0.86 (0.44, 1.70) | 1.28 (0.47, 3.50) | | |
| VEGFR G$^{889}$A | | | | | | |
| GG | 140 (54.4) | 388 (59.3) | 1.00 | 1.00 | 0.463 | 0.315 |
| GA | 76 (39.8) | 299 (35.0) | 1.24 (0.88, 1.74) | 1.08 (0.69, 1.70) | | |
| AA | 11 (5.8) | 37 (5.7) | 1.11 (0.55, 2.25) | 0.98 (0.38, 2.53) | | |
| GA + AA | 87 (45.6) | 266 (40.7) | 1.22 (0.88, 1.69) | 1.07 (0.69, 1.65) | | |
| VEGFR$^{IVS6+54}$ | | | | | | |
| CC | 65 (34.8) | 225 (34.3) | 1.00 | 1.00 | 0.338 | 0.392 |
| CT | 93 (49.7) | 299 (45.6) | 1.08 (0.75, 1.54) | 1.08 (0.67, 1.75) | | |
| TT | 29 (15.5) | 132 (20.1) | 0.76 (0.47, 1.24) | 0.73 (0.38, 1.40) | | |
| CT + TT | 122 (65.2) | 431 (65.7) | 0.98 (0.70, 1.38) | 0.98 (0.62, 1.54) | | |

TABLE 3-continued

Association between Prostate Cancer Risk and Single Gene Effects

| Genotype | Case n (%) | Control n (%) | OR (95% CI) | Adj OR (95% CI)† | P-value†† | P-trend‡ |
|---|---|---|---|---|---|---|
| VEGRF T$^{1416}$A | | | | | | |
| TT | 154 (81.5) | 545 (83.1) | 1.00 | 1.00 | 0.857 | 0.645 |
| TA | 34 (18.0) | 107 (16.3) | — | — | | |
| AA | 1 (0.5) | 4 (0.6) | — | — | | |
| TA + AA | 35 (18.5) | 111 (16.9) | 1.12 (0.73, 1.70) | 0.54 (0.28, 1.05) | | |
| VEGFR G$^{IVS25-92}$A | | | | | | |
| GG | 87 (46.0) | 293 (45.6) | 1.00 | 1.00 | 0.068 | 0.332 |
| AG | 68 (36.0) | 272 (42.4) | 0.84 (0.59, 1.20) | 0.82 (0.50, 1.35) | | |
| AA | 34 (18.0) | 77 (12.0) | 1.49 (0.93, 2.38) | 1.44 (0.77, 2.71) | | |
| AG + AA | 102 (54.0) | 349 (54.4) | 0.98 (0.71, 1.36) | 0.97 (0.62, 1.53) | | |

†Associations were determined using multivariate LR models to estimate the risk of developing PCa using IL10 (−1082 G/G, −819CC, −592CC), IL-10R (−153 G/G, −109 G/G, 241 G/G), TGFβ-1 (−896 T/T, 509 C/C), TGFβ1+195 A/A, VEGF (2482 C/C, 2578 A/A), VEGFR (889 G/G, IVS25-92 G/G, IVS6+54 A/A) as the reference genotypes.
††Risk estimates adjusted for age (continuous variable) and prostate specific antigen (continuous variable).
†††Differences in the frequency of variant and referent genotypes between cases and controls were determined using the chi-square test of association and a significance level of 0.05.

TABLE 4

Relationship between VEGF C$^{2482}$T and Disease Progression.

| Gene/SNP | Unadjusted OR (95% CI) † | Adjusted OR (95% CI) †† | P-value††† |
|---|---|---|---|
| VEGF C$^{2482}$T | | | |
| CC | 1.00 | 1.00 | 0.017 |
| CT + TT | 2.12 (0.92-5.10) | 3.12 (1.23-7.92) | |

† Associations were determined using multivariate LR models to estimate the risk of developing aggressive prostate cancer (tumor grade >8)PCa using VEGF 2482 C/C as the reference genotypes.
†† Risk estimates adjusted for age (continuous variable) and prostate specific antigen (continuous variable).
†††P-value adjusted for age and PSA were calculated using logistic regression modeling comparing the genotype profile of men with aggressive disease to those with non-aggressive disease with a significance level of <0.05.

TABLE 5

Multi-Dimensionality Reduction Models for Angiogenesis-Related Markers.

| Best Model | Cross Validation Consistency (CVC) | Average Testing Accuracy | Permutation Testing P-value |
|---|---|---|---|
| One Factor | | | |
| IL-10-1082 | 6/10 | 0.504 | >0.10 |
| Two Factor | | | |
| VEGF 2482 VEGFR_54 | 10/10 | 0.584 | 0.04 |

Interaction Entropy Graphs.

Following identification of high risk loci using MDR, the interpretation of the relationship among the selected variables was facilitated using interaction entropy algorithms. A graphical model was constructed that describes the percent entropy that is explained by each Angiogenesis-Related SNP or a combination of two loci within the study population. Positive percent entropy indicates information gain or synergy. However, negative percent indicates redundancy or lack of information gain. Schematic coloration used in the visualization tools represents a continuum from synergy (i.e., non-additive) to redundancy. The colors range from red representing a high degree of synergy (positive information gain), orange a lesser degree, and gold representing independence and a midway point between synergy and redundancy. On the other hand, green represents redundancy. Notably, as indicated in the hierarchical interaction graph (FIG. 1), the VEGF 2482/VEGFR IVS6+54 SNP pair had the highest degree of entropy percentage (0.99%) when compared to individual markers and pairwise SNP combinations. Thus, VEGF 2482 combined with VEGFR IVS6+54 provide more information in relation to prostate cancer risk relative to other individual loci or SNP pairs.

REFERENCE LIST

1. Lichtenstein P, Holm N V, Verkasalo P K, Iliadou A, Kaprio J, Koskenvuo M, Pukkala E, Skytthe A, Hemminki K Environmental and heritable factors in the causation of cancer—analyses of cohorts of twins from Sweden, Denmark, and Finland. N Engl J Med 2000; 343:78-85.
2. Michaud D S, Daugherty S E, Berndt S I, Platz E A, Yeager M, Crawford E D, Hsing A, Huang W Y, Hayes R B. Genetic polymorphisms of interleukin-1B (IL-1B), IL-6, IL-8, and IL-10 and risk of prostate cancer. Cancer Res 2006; 66:4525-4530.
3. Tavtigian S V, Simard J, Teng D H, Abtin V, Baumgard M, Beck A, Camp N J, Carillo A R, Chen Y, Dayananth P, Desrochers M, Dumont M, Farnham J M, Frank D, Frye C, Ghaffari S, Gupte J S, Hu R, Iliev D, Janecki T, Kort E N, Laity K E, Leavitt A, Leblanc G, Arthur-Morrison J, Pederson A, Penn B, Peterson K T, Reid J E, Richards S, Schroeder M, Smith R, Snyder S C, Swedlund B, Swensen J, Thomas A, Tranchant M, Woodland A M, Labrie F, Skolnick M H, Neuhausen S, Rommens J, Cannon-Albright L A. A candidate prostate cancer susceptibility gene at chromosome 17p. Nat Genet. 2001; 27:172-180.
4. Gibbs M, Stanford J L, McIndoe R A, Jarvik G P, Kolb S, Goode E L, Chakrabarti L, Schuster E F, Buckley V A, Miller E L, Brandzel S, Li S, Hood L, Ostrander E A. Evidence for a rare prostate cancer-susceptibility locus at chromosome 1p36. Am J Hum Genet. 1999; 64:776-787.
5. Xu J, Meyers D, Freije D, Isaacs S, Wiley K, Nusskern D, Ewing C, Wilkens E, BujnovPCaky P, Bova G S, Walsh P, Isaacs W, Schleutker J, Matikainen M, Tammela T, Visakorpi T, Kallioniemi O P, Berry R, Schaid D, French A, McDonnell S, Schroeder J, Blute M, Thibodeau S, Gronberg H, Emanuelsson M, Damber J E, Bergh A, Jonsson B A, Smith J, Bailey-Wilson J, Carpten J, Stephan D, Gillanders E, Amundson I, Kainu T, Freas-Lutz D, Baffoe-Bonnie A, Van A A, Sood R, Collins F, Brownstein M, Trent J. Evidence for a prostate cancer susceptibility locus on the X chromosome. Nat Genet. 1998; 20:175-179.
6. Berthon P, Valeri A, Cohen-Akenine A, Drelon E, Paiss T, Wohr G, Latil A, Millasseau P, Mellah I, Cohen N, Blanche H, Bellane-Chantelot C, Demenais F, Teillac P, Le DA, de P R, Hautmann R, Chumakov I, Bachner L, Maitland N J, Lidereau R, Vogel W, Fournier G, Mangin P, Cussenot O., Predisposing gene for early-onset prostate cancer, localized on chromosome 1q42.2-43. Am J Hum Genet. 1998; 62:1416-1424.
7. Smith J R, Freije D, Carpten J D, Gronberg H, Xu J, Isaacs S D, Brownstein M J, Bova G S, Guo H, BujnovPCaky P, Nusskem D R, Damber J E, Bergh A, Emanuelsson M, Kallioniemi O P, Walker-Daniels J, Bailey-Wilson J E, Beaty T H, Meyers D A, Walsh P C, Collins F S, Trent J M, Isaacs W B. Major susceptibility locus for prostate cancer on chromosome 1 suggested by a genome-wide search. Science 1996; 274:1371-1374.
8. Ford D, Easton D F, Bishop D T, Narod S A, Goldgar D E. Risks of cancer in BRCA1-mutation carriers. Breast Cancer Linkage Consortium. Lancet 1994; 343:692-695.
9. Richter G, Kruger-Krasagakes S, Hein G, Huls C, Schmitt E, Diamantstein T, Blankenstein T. Interleukin 10 transfected into Chinese hamster ovary cells prevents tumor growth and macrophage infiltration. Cancer Res 1993; 53:4134-4137.
10. Nabioullin R, Sone S, Mizuno K, Yano S, Nishioka Y, Haku T, Ogura T. Interleukin-10 is a potent inhibitor of tumor cytotoxicity by human monocytes and alveolar macrophages. J Leukoc Biol 1994; 55:437-442.
11. Stearns M E, Wang M. Antimestatic and antitumor activities of interleukin 10 in transfected human prostate PC-3 mL clones: Orthotopic growth in severe combined immunodeficient mice. Clin Cancer Res 1998; 4:2257-2263.
12. Huang S, Xie K, Bucana C D, Ullrich S E, Bar-Eli M. Interleukin 10 suppresses tumor growth and metastasis of human melanoma cells: potential inhibition of angiogenesis. Clin Cancer Res 1996; 2:1969-1979.
13. Sato T, McCue P, Masuoka K, Salwen S, Lattime E C, Mastrangelo M J, Berd D. Interleukin 10 production by human melanoma. Clin Cancer Res 1996; 2:1383-1390.
14. Balkwill F, Mantovani A. Inflammation and cancer: back to Virchow? Lancet 2001; 357:539-545.
15. Derynck R, Akhurst R J, Balmain A. TGF-beta signaling in tumor suppression and cancer progression. Nat Genet. 2001; 29:117-129.
16. Leung D W, Cachianes G, Kuang W J, Goeddel D V, Ferrara N. Vascular endothelial growth factor is a secreted angiogenic mitogen. Science 1989; 246:1306-1309.
17. Tischer E, Mitchell R, Hartman T, Silva M, Gospodarowicz D, Fiddes J C, Abraham J A. The human gene for vascular endothelial growth factor. Multiple protein forms are encoded through alternative exon splicing. J Biol Chem 1991; 266:11947-11954.
18. Claffey K P, Robinson G S. Regulation of VEGF/VPF expression in tumor cells: consequences for tumor growth and metastasis. Cancer Metastasis Rev 1996; 15:165-176.
19. Houck K A, Ferrara N, Winer J, Cachianes G, Li B, Leung D W. The vascular endothelial growth factor family: identification of a fourth molecular species and characterization of alternative splicing of RNA. Mol Endocrinol 1991; 5:1806-1814.
20. Poltorak Z, Cohen T, Sivan R, Kandelis Y, Spira G, Vlodaysky I, Keshet E, Neufeld G. VEGF145, a secreted vascular endothelial growth factor isoform that binds to extracellular matrix. J Biol Chem 1997; 272:7151-7158.
21. Lei J, Jiang A, Pei D. Identification and characterization of a new splicing variant of vascular endothelial growth factor: VEGF183. Biochim Biophys Acta 1998; 1443:400-406.
22. Robinson C J, Stringer S E. The splice variants of vascular endothelial growth factor (VEGF) and their receptors. J Cell Sci 2001; 114:853-865.
23. Lu H, Shu X O, Cui Y, Kataoka N, Wen W, Cai Q, Ruan Z X, Gao Y T, Zheng W. Association of genetic polymorphisms in the VEGF gene with breast cancer survival. Cancer Res 2005; 65:5015-5019.
24. Ferrara N. VEGF and the quest for tumour angiogenesis factors. Nat Rev Cancer 2002; 2:795-803.
25. Ferrara N, Gerber H P, LeCouter J. The biology of VEGF and its receptors. Nat Med 2003; 9:669-676.
26. Waltenberger J, Claesson-Welsh L, Siegbahn A, Shibuya M, Heldin C H. Different signal transduction properties of KDR and Flt1, two receptors for vascular endothelial growth factor. J Biol Chem 1994; 269:26988-26995.
27. Quinn T P, Peters K G, De V C, Ferrara N, Williams L T. Fetal liver kinase 1 is a receptor for vascular endothelial growth factor and is selectively expressed in vascular endothelium. Proc Natl Acad Sci USA 1993; 90:7533-7537.
28. Peyromaure M, Camparo P, Badoual C, Descazeaud A, nh-Xuan A T. The expression of vascular endothelial growth factor is associated with the risk of cancer progression after radical prostatectomy. BJU Int 2007; 99:1150-1153.
29. Green M M, Hiley C T, Shanks J H, Bottomley I C, West C M, Cowan R A, Stratford I J. Expression of vascular endothelial growth factor (VEGF) in locally invasive prostate cancer is prognostic for radiotherapy outcome. Int J Radiat Oncol Biol Phys 2007; 67:84-90.
30. Packer B R, Yeager M, Burdett L, Welch R, Beerman M, Qi L, Sicotte H, Staats B, Acharya M, Crenshaw A, Eckert A, Puri V, Gerhard D S, Chanock S J. SNP500Cancer: a public resource for sequence validation, assay development, and frequency analysis for genetic variation in candidate genes. Nucleic Acids Res 2006; 34:D617-D621.
31. Giri V N, Egleston B, Ruth K, Uzzo R G, Chen D Y, Buyyounouski M, Raysor S, Hooker S, Torres J B, Ramike T, Mastalski K, Kim T Y, Kitties R. Race, genetic West African ancestry, and prostate cancer prediction by prostate-specific antigen in prospectively screened high-risk men. Cancer Prey Res (Phila Pa.) 2009; 2:244-250.
32. Ritchie M D, Hahn L W, Roodi N, Bailey L R, Dupont W D, Parl F F, Moore JH. Multifactor-dimensionality reduction reveals high-order interactions among estrogen-metabolism genes in sporadic breast cancer. Am J Hum Genet. 2001; 69:138-147.
33. Moore J H. Computational analysis of gene-gene interactions using multifactor dimensionality reduction. Expert Rev Mol Diagn 2004; 4:795-803.
34. See the epistasis website. 2006. 7-11-0006.
35. Jakulin A, Bratko I. Analyzing attribute dependencies. In Lavrac N, Gamberger D, Blockeel H and Todorovski L (eds.) PKDD 2003. Cavtat, Croatia.: Springer-Verlag, 2003; pp. 229-240-240.
36. Demosar J, Zupan B. Orange: From Experimental Machine Learning to Interactive Data Mining, White Paper. 2004.
37. Ritchie M D, Hahn L W, Moore J H. Power of multifactor dimensionality reduction for detecting gene-gene interactions in the presence of genotyping error, missing data, phenocopy, and genetic heterogeneity. Genet Epidemiol 2003; 24:150-157.

38. Andrew A S, Nelson H H, Kelsey K T, Moore J H, Meng A C, Casella D P, Tosteson T D, Schned A R, Karagas M R. Concordance of multiple analytical approaches demonstrates a complex relationship between DNA repair gene SNPs, smoking, and bladder cancer susceptibility. Carcinogenesis 2005; 1030-1037.
39. Jakulin A, Bratko I, Smrike D, Demsar J, Zupan B. Attribute interactions in medical data analysis. Protarus: Cyprus, 2003; pp. 229-238-238.
40. Moore, J. H., Barney, N., and White, B. C. Solving complex problems in human genetics using genetic programming: The importance of theorist-practitioner-computer interaction. 69-85. 2008.
41. Moore, J. H. and White, B. C. Tuning ReliefF for genome-wide genetic analysis. 166-175. 2007.
42. Moore, J. H. and White, B. C. Genome-wide genetic analysis using genetic programming The critical need for expert knowledge. 11-28. 2007.
43. Moore, J. H. and White, B. C. Exploiting expert knowledge in genetic programming for genome-wide genetic analysis. 969-977. 2006.
44. See the NCBI website.
45. Kaya A, Ciledag A, Gulbay B E, Poyraz B M, Celik G, Sen E, Savas H, Savas I. The prognostic significance of vascular endothelial growth factor levels in sera of non-small cell lung cancer patients. Respir Med 2004; 98:632-636.
46. Sfar S, Hassen E, Saad H, Mosbah F, Chouchane L. Association of VEGF genetic polymorphisms with prostate carcinoma risk and clinical outcome. Cytokine 2006; 35:21-28.
47. Kollermann J, Helpap B. Expression of vascular endothelial growth factor (VEGF) and VEGF receptor Flk-1 in benign, premalignant, and malignant prostate tissue. Am J Clin Pathol 2001; 116:115-121.
48. Plaisance V, Niederhauser G, Azzouz F, Lenain V, Haefliger J A, Waeber G, Abderrahmani A. The repressor element silencing transcription factor (REST)-mediated transcriptional repression requires the inhibition of Sp1. J Biol Chem 2005; 280:401-407.
49. Kim C S, Choi H S, Hwang C K, Song K Y, Lee B K, Law P Y, Wei L N, Loh H H. Evidence of the neuron-restrictive silencer factor (NRSF) interaction with Sp3 and its synergic repression to the mu opioid receptor (MOR) gene. Nucleic Acids Res 2006; 34:6392-6403.
50. Genomatix website. 2009.
51. Carmeliet P. Angiogenesis in life, disease and medicine. Nature 2005; 438:932-936.
52. Carmeliet P, Jain R K. Angiogenesis in cancer and other diseases. Nature 2000; 407:249-257.
53. Zahnow C A. CCAAT/enhancer-binding protein beta: its role in breast cancer and associations with receptor tyrosine kinases. Expert Rev Mol Med 2009; 11:e12.
54. Howell W M, Turner S J, Bateman A C, Theaker J M. IL-10 promoter polymorphisms influence tumour development in cutaneous malignant melanoma. Genes Immun 2001; 2:25-31.
55. Turner D M, Williams D M, Sankaran D, Lazarus M, Sinnott P J, Hutchinson I V. An investigation of polymorphism in the interleukin-10 gene promoter. Eur J Immunogenet 1997; 24:1-8.
56. Dunning A M, Ellis P D, McBride S, Kirschenlohr H L, Healey C S, Kemp P R, Luben R N, Chang-Claude J, Mannermaa A, Kataja V, Pharoah P D, Easton D F, Ponder B A, Metcalfe J C. A transforming growth factorbeta1 signal peptide variant increases secretion in vitro and is associated with increased incidence of invasive breast cancer. Cancer Res 2003; 63:2610-2615.
57. Yokota M, Ichihara S, Lin T L, Nakashima N, Yamada Y. Association of a T29->C polymorphism of the transforming growth factor-beta1 gene with genetic susceptibility to myocardial infarction in Japanese. Circulation 2000; 101:2783-2787.
58. Grainger D J, Heathcote K, Chiano M, Snieder H, Kemp P R, Metcalfe J C, Carter N D, Spector T D. Genetic control of the circulating concentration of transforming growth factor type beta1. Hum Mol Genet. 1999; 8:93-97.
59. Ewart-Toland A, Chan J M, Yuan J, Balmain A, Ma J. A gain of function TGFB1 polymorphism may be associated with late stage prostate cancer. Cancer Epidemiol Biomarkers Prev 2004; 13:759-764.
60. Lambrechts D, Storkebaum E, Morimoto M, Del-Favero J, Desmet F, Marklund S L, Wyns S, Thijs V, Andersson J, van M, I, Al-Chalabi A, Bornes S, Musson R, Hansen V, Beckman L, Adolfsson R, Pall H S, Prats H, Vermeire S, Rutgeerts P, Katayama S, Awata T, Leigh N, Lang-Lazdunski L, Dewerchin M, Shaw C, Moons L, Vlietinck R, Morrison K E, Robberecht W, Van B C, Collen D, Andersen P M, Carmeliet P. VEGF is a modifier of amyotrophic lateral sclerosis in mice and humans and protects motoneurons against ischemic death. Nat Genet. 2003; 34:383-394.
61. Shahbazi M, Fryer A A, Pravica V, Brogan I J, Ramsay H M, Hutchinson I V, Harden P N. Vascular endothelial growth factor gene polymorphisms are associated with acute renal allograft rejection. J Am Soc Nephrol 2002; 13:260-264.
62. Park H W, Lee J E, Shin E S, Lee J Y, Bahn J W, Oh H B, Oh S Y, Cho S H, Moon H B, Min K U, Elias J A, Kim Y Y, Kim Y K. Association between genetic variations of vascular endothelial growth factor receptor 2 and atopy in the Korean population. J Allergy Clin Immunol 2006; 117:774-779.
63. Renner W, Kotschan S, Hoffmann C, Obermayer-Pietsch B, Pilger E. A common 936 C/T mutation in the gene for vascular endothelial growth factor is associated with vascular endothelial growth factor plasma levels. J Vasc Res 2000; 37:443-448.
64. Krippl P, Langsenlehner U, Renner W, Yazdani-Biuki B, Wolf G, Wascher T C, Paulweber B, Haas J, Samonigg H. A common 936 C/T gene polymorphism of vascular endothelial growth factor is associated with decreased breast cancer risk. Int J Cancer 2003; 106:468-471.
65. Krippl P, Langsenlehner U, Renner W, Yazdani-Biuki B, Wolf G, Wascher T C, Paulweber B, Bahadori B, Samonigg H. The L10P polymorphism of the transforming growth factor-beta 1 gene is not associated with breast cancer risk. Cancer Lett 2003; 201:181-184.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a subject's risk of developing prostate cancer (PCa), the method comprising:
   obtaining a sample comprising DNA of the subject; and
   determining the identity of a genetic profile comprising alleles at VEGF 2482 (rs3025040) and at VEGFR IVS6+54 (rs7692791) in the subject,
wherein the presence of VEGF 2482 C>T and VEGFR IVS6+54 G>A indicates that the subject has an increased risk of developing PCa.

2. The method of claim 1, wherein the sample is obtained from the subject by a health care provider.

3. The method of claim 1, wherein the sample is provided by the subject without the assistance of a health care provider.

4. The method of claim 1, further comprising determining the presence or absence of one or more additional markers associated with risk of developing PCa.

5. The method of claim 1, wherein the subject is a human.

6. The method of claim 1, wherein the subject is a patient having one or more risk factors for PCa.

7. The method of claim 6, wherein the risk factors associated with PCa include one or more of: age; race/ethnicity; nationality; family history; diet; obesity; lack of exercise; inflammation of the prostate; infection; vasectomy; and the presence of other genes or genetic variants associated with increased risk of PCa.

8. The method of claim 7, wherein the subject is of African descent.

9. The method of claim 7, wherein the subject is African-American.

10. The method of claim 7, wherein the subject has one or more of a grandparent, parent, uncle or aunt, sibling, or child who has or had PCa.

11. The method of claim 1, further comprising administering a treatment to a subject identified as being at increased risk for developing PCa.

12. The method of claim 11, wherein the treatment is administration of an inhibitor of VEGF signaling.

13. The method of claim 1, further comprising stratifying a subject population for a clinical trial based on the identity of alleles at VEGF 2482 (rs3025040) and at VEGFR IVS6+54 (rs7692791).

* * * * *